United States Patent [19]

Jang

[11] Patent Number: 4,744,366
[45] Date of Patent: May 17, 1988

[54] CONCENTRIC INDEPENDENTLY INFLATABLE/DEFLATABLE MULTIPLE DIAMETER BALLOON ANGIOPLASTY CATHETER SYSTEMS AND METHOD OF USE

[76] Inventor: G. David Jang, 636 Golden West Dr., Redlands, Calif. 92373

[21] Appl. No.: 905,790

[22] Filed: Sep. 10, 1986

[51] Int. Cl.⁴ .............................................. A61M 29/02
[52] U.S. Cl. ...................................... 128/344; 604/101
[58] Field of Search ...................... 128/344, 325, 348.1, 128/207.15, 10; 604/96–103

[56] References Cited

U.S. PATENT DOCUMENTS

| | | | |
|---|---|---|---|
| 1,690,995 | 11/1928 | Pratt | 128/344 |
| 2,799,273 | 7/1957 | Oddo | 128/325 |
| 3,045,677 | 7/1962 | Wallace | 128/349 |
| 3,211,152 | 10/1965 | Stern | 128/207.15 |
| 4,091,816 | 5/1978 | Elam | 128/351 |
| 4,195,637 | 4/1980 | Gruntzig et al. | 128/348 |
| 4,295,464 | 10/1981 | Shihata | 128/1 |
| 4,327,736 | 5/1982 | Inoue | 128/349 |
| 4,328,056 | 5/1982 | Snooks | 604/96 |
| 4,338,942 | 7/1982 | Fogarty | 128/325 |
| 4,404,971 | 9/1983 | LeVeen et al. | 128/348 |
| 4,423,725 | 1/1984 | Baran et al. | 128/207 |
| 4,430,076 | 2/1984 | Harris | 604/96 |
| 4,445,892 | 5/1984 | Hussein et al. | 604/101 |
| 4,456,011 | 6/1984 | Warnecke | 128/325 |
| 4,520,823 | 6/1985 | LeVeen et al. | 128/348 |
| 4,527,549 | 7/1985 | Gabbay | 128/1 |
| 4,546,759 | 10/1985 | Solar | 128/1 |
| 4,554,929 | 11/1985 | Samson et al. | 128/772 |
| 4,571,240 | 2/1986 | Samson et al. | 604/96 |
| 4,573,470 | 3/1986 | Samson et al. | 128/344 |
| 4,573,966 | 3/1986 | Weikl et al. | 604/53 |
| 4,581,017 | 4/1986 | Sahota | 604/102 |
| 4,655,746 | 4/1987 | Daniels et al. | 604/53 |

FOREIGN PATENT DOCUMENTS 0654214 2/1986 Switzerland .................... 604/101

OTHER PUBLICATIONS

*Angioplasty,* G. David Jang, (1986).

Primary Examiner—Dalton L. Truluck
Assistant Examiner—Frank Wilkens
Attorney, Agent, or Firm—Knobbe, Martens, Olson & Bear

[57] ABSTRACT

Disclosed is a catheter for performing balloon angioplasty comprising concentric, independently inflatable/deflatable balloons, each balloon having a different diameter. The balloons are capable of withstanding pressures in excess of 100 psi and are non-elastomeric and imperforate. Also disclosed is a method for performing balloon angioplasty by advancing a balloon catheter of the type disclosed into a stenosis inside a blood vessel, inflating a first balloon to partially dilate the stenosis, advancing a second balloon into the partially dilated stenosis, wherein the diameter of the second balloon is greater than the diameter of the first balloon, and inflating the second balloon to further dilate the stenosis. Also disclosed is a method for performing balloon angioplasty with a catheter of the type disclosed herein, by positioning a first balloon inside a first stenosis in a blood vessel and inflating a first balloon to dilate the first stenosis, and positioning a second balloon inside a second stenosis in a blood vessel and inflating the second balloon to dilate the second stenosis, wherein the diameter of the first balloon is different from the diameter of the second balloon. The method further may include positioning a third balloon inside a third stenosis in a blood vessel and inflating the third balloon to dilate the third stenosis, wherein the diameter of the third balloon is different from the diameters of the first and second balloons.

52 Claims, 8 Drawing Sheets

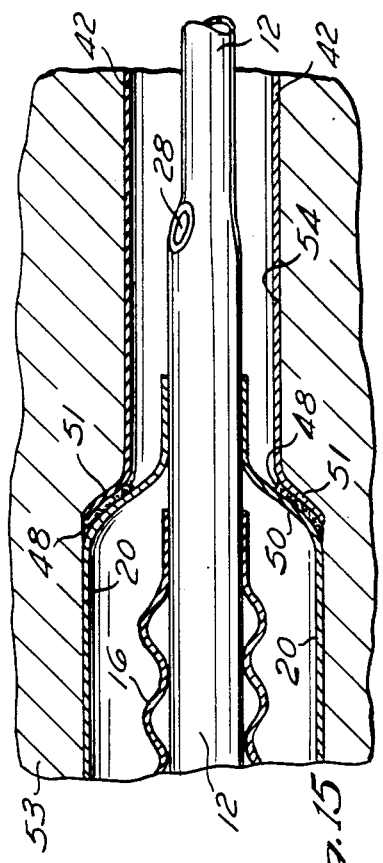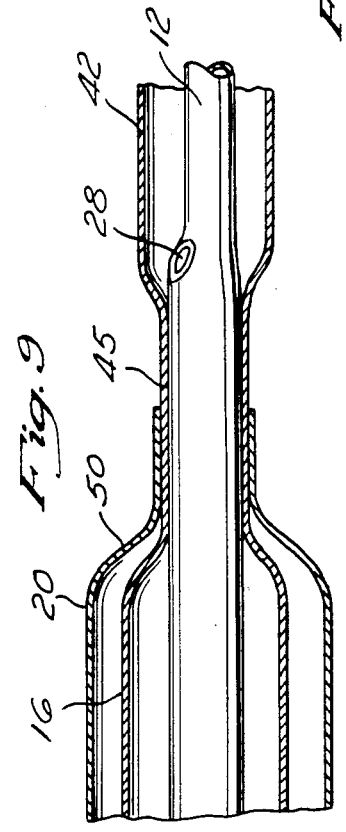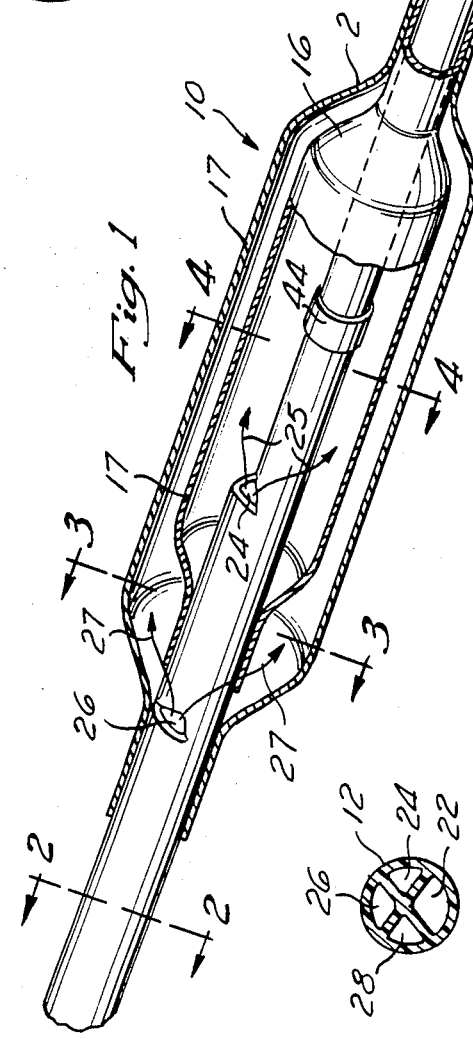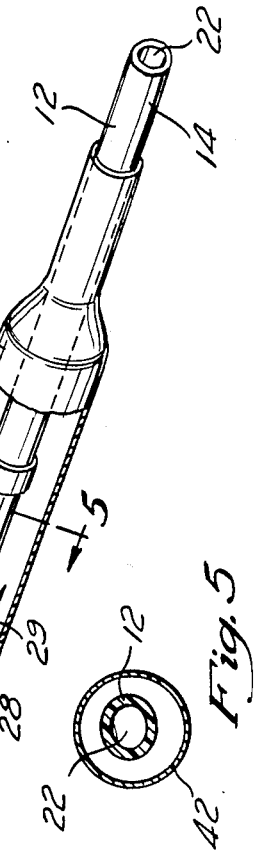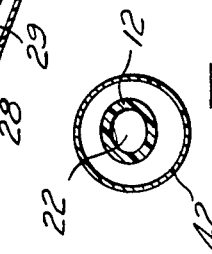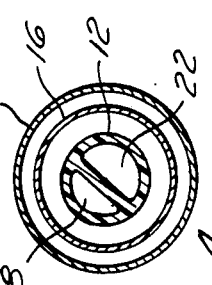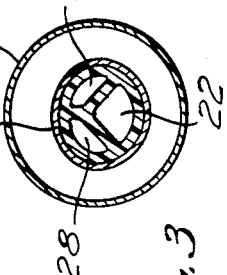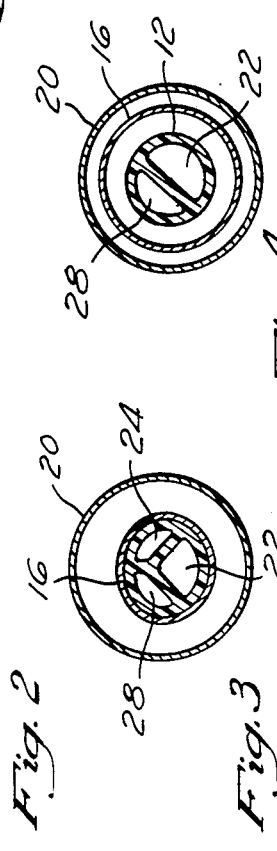

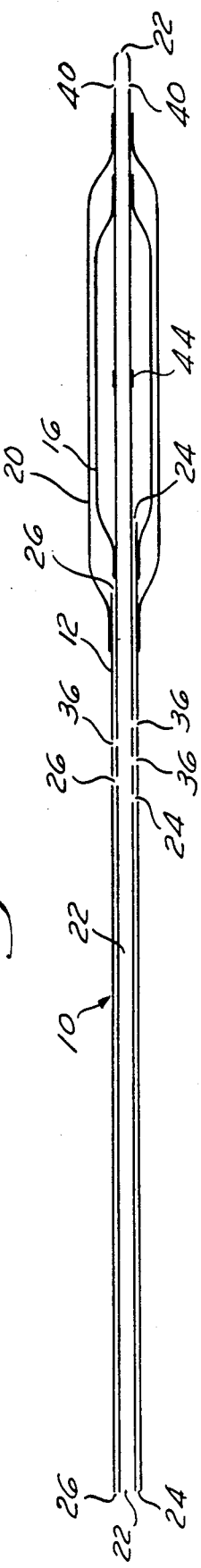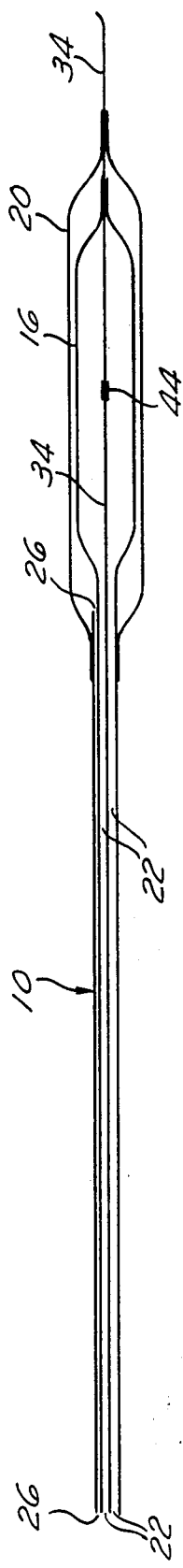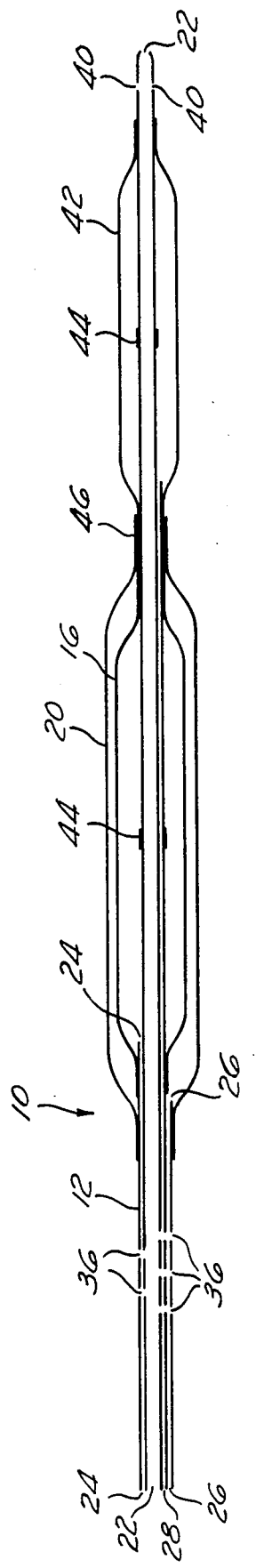

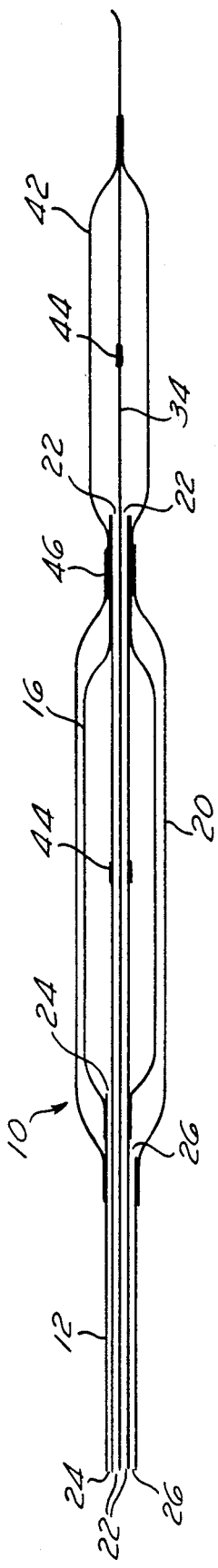
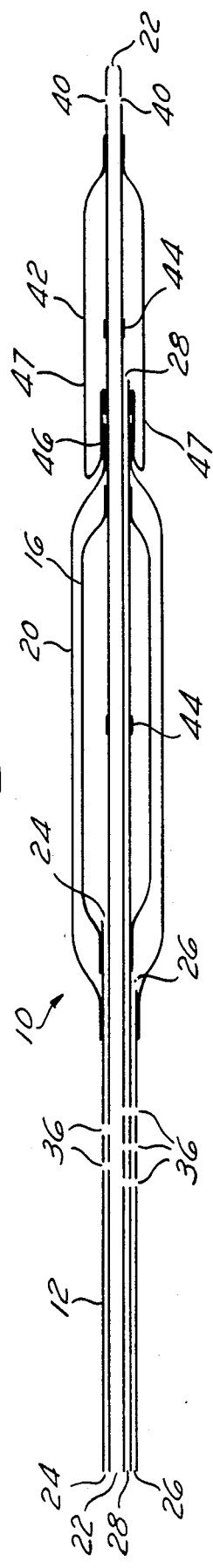
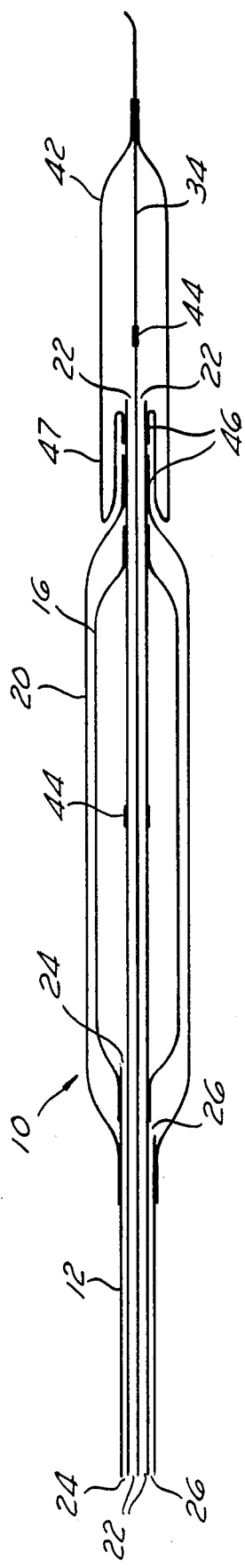
Fig.10
Fig.11
Fig.13

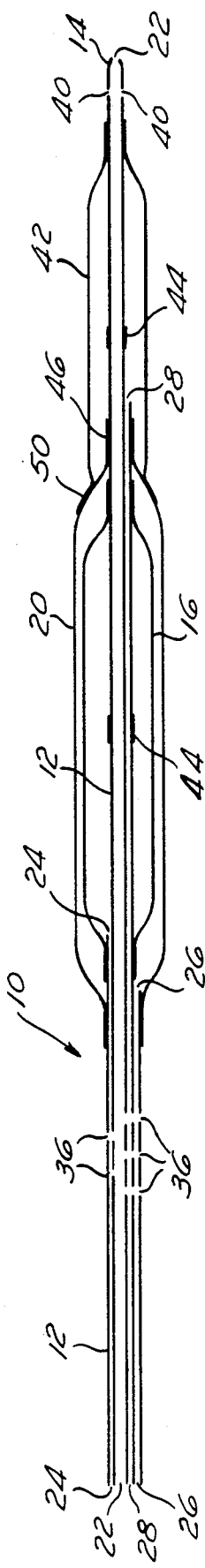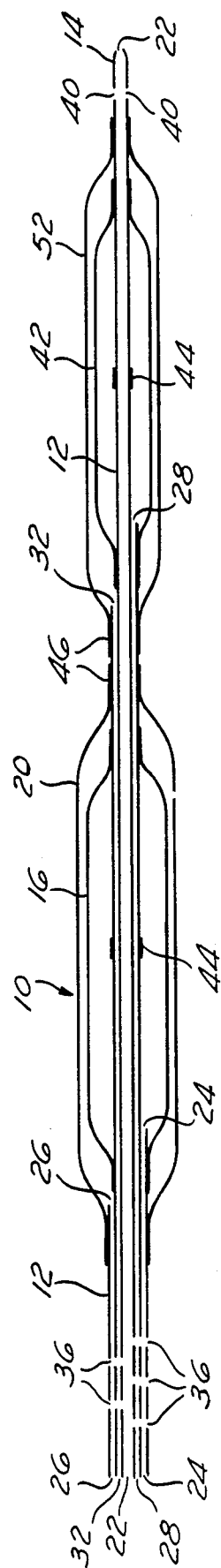

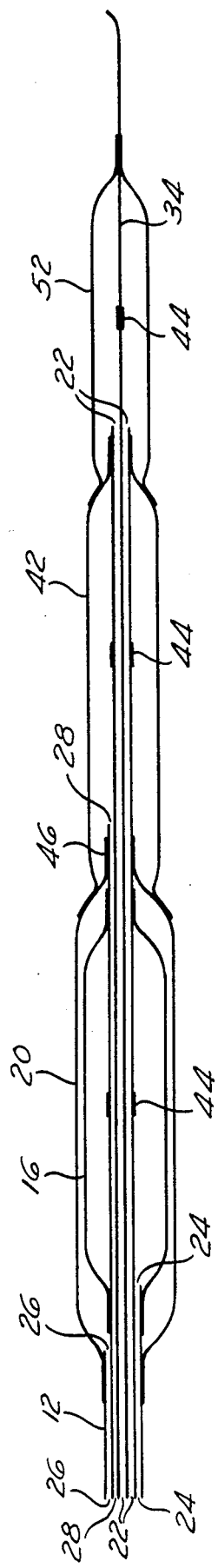
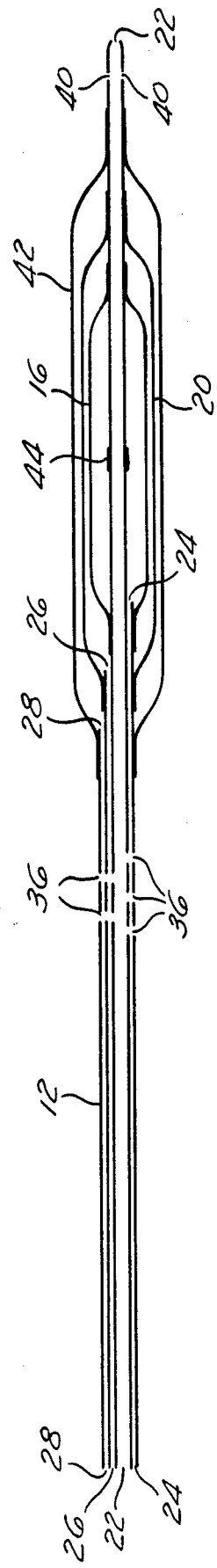
Fig. 20
Fig. 21

CONCENTRIC INDEPENDENTLY INFLATABLE/DEFLATABLE MULTIPLE DIAMETER BALLOON ANGIOPLASTY CATHETER SYSTEMS AND METHOD OF USE

BACKGROUND OF THE INVENTION

This invention relates to balloon angioplasty, and particularly to angioplasty catheter systems utilizing multiple balloons and to angioplasty procedures utilizing those catheters.

Coronary angioplasty has emerged as the only viable present alternative to bypass surgery for revascularization of stenotic and occluded coronary arteries. Although transluminal angioplasty has application in peripheral artery disease, it is most widely used in the treatment of coronary artery disease. Unlike bypass surgery, percutaneous angioplasty does not require general anesthesia, cutting of the chest wall, extracorporeal perfusion, or transfusion of blood. Percutaneous coronary angioplasty is not only less invasive and less traumatic to the patient, it is also less expensive because the angioplasty patient will have a shorter hospital stay and shorter post-procedure recovery time.

Percutaneous transluminal angioplasty is performed by making a skin puncture with a specially-designed needle in one of the groins, and then introducing a guiding catheter (typically 8 or 9 French size) into the aorta and coronary artery orifice. A smaller caliber catheter which has a built-in inflatable and deflatable balloon of predetermined size and diameter is passed through the guiding catheter which is positioned in the opening of a target artery. This balloon catheter (with the balloon totally deflated by negative pressure) is advanced inside the target artery toward the point of obstruction that needs to be dilated. With the balloon portion of the catheter properly positioned inside the obstructed segment of the artery, under X-ray fluoroscopic observation, the balloon is inflated by injecting contrast media mixed with saline at a pressure sufficient to overcome the resistance of the atherosclerotic plaque of the obstructed segment.

During the guiding catheter manipulation and especially while the balloon catheter is being advanced into the narrowed segment of the artery, X-ray fluoroscopy is used extensively. However, because one cannot ordinarily see the anatomy of an artery under X-ray fluoroscopy, contrast material is used. When contrast media is injected into an artery, details of the arterial anatomy are briefly visible until the contrast material flows away with the blood flow through the artery. Radiographic arteriograms are recorded during that brief moment of visualization. If the anatomic structures are complex and negotiating a particular arterial channel with the balloon catheter is difficult, frequent contrast injections during the procedure are necessary. However, there are limits to the amount of contrast material one can use in a given patient. For instance, the upper limit of Renografin-76 in a normal individual is approximately 3 c.c.'s per kilogram of body weight. The tolerance of a physically-ill individual may be substantially less. Excessive amounts of contrast material can be toxic to the kidneys, liver, and brain.

By inflating the balloon in the stenosis multiple times over a period of between 20–30 seconds and one or two minutes (allowing blood flow between inflations), the desired dilation of the obstructed segment of the artery can be achieved. When the desired results have been obtained by balloon inflations, the guiding catheter and the balloon catheter (with the balloon completely deflated with negative pressure) are withdrawn from the artery and the procedure is successfully terminated.

Atherosclerotic coronary artery disease is not curable. Both bypass surgery and balloon angioplasty are considered palliative treatments. Recurrence of disease after bypass surgery or coronary angioplasty is prevalent, and repeat procedures are not uncommon due to the nature of the disease. A patient may initially develop single-vessel coronary artery disease and then slowly progress into multiple-vessel disease over the years. Medications, bypass surgery or angioplasty do help to relieve the symptoms, but they generally cannot prevent a gradual progression of the disease.

Because the cost of bypass surgery is 2 to 2.5 times the cost of angioplasty, and because bypass surgery is more invasive, more traumatic, requiring longer hospital stays and longer post-operative recuperation, future demand for angioplasty is expected to grow as physician skill and equipment technology expands. It has been estimated that the number of coronary artery angioplasties performed in the U.S. will double or triple to 450,000 or 500,000 cases per year by the early to mid 1990's. It also has been estimated that the numer of multiple-vessel angioplasty cases will be from 2 to 2.5 times the number of single-vessel angioplasty cases. This will be a dramatic change from the situation in 1986 in which 70 to 80 percent of the coronary angioplasty cases are single-vessel dilations. The expected future growth of multi-vessel coronary angioplasty has serious technical and patient care implications. Present-day coronary angioplasty technology is based on the original single balloon concept which was designed to tackle single-vessel disease and thus single-vessel dilations. However, the single balloon technology is inadequate to meet the requirements of most multi-vessel disease situations.

During a typical coronary angioplasty, most of the procedure time is spent in certain preliminary steps that are necessary before the balloon can be inflated inside the obstructed segment of a target artery. In fact, the real job of dilating a vessel takes less than 20 percent of the total procedure time. The preliminary steps include patient (aseptic) preparation, groin preparation and needle puncture, insertion of the guidewire into the artery to introduce the guiding catheter, arterial heparinization, manipulation of the guiding catheter to cannulate the target coronary orifice, preliminary arteriography using contrast media injection into the artery and taking radiographic cine. Moreover, the balloon catheter must be prepared before it can be introduced into the target artery through the lumen of the guiding catheter. Preparation of the balloon catheter takes a minimum of 15–20 minutes. X-ray fluoroscopy and contrast media are extensively used during the guiding catheter and balloon catheter manipulations, especially when the balloon tip is being manipulated through the inside of the artery toward an obstructed segment which needs to be reopened by the balloon tip. Sometimes, the majority of the procedure time and the limits of the total allowable contrast volume are used up at this phase of a procedure. It is clear from the medical literature that the longer the procedure, the greater the risk of complications during cardiac catheterization. Likewise, the larger the volume of contrast material, the greater the chance of kidney failure or tissue toxicity, including brain and/or liver damage.

The size and diameter of the balloon to be used in a transluminal angioplasty should be approximately matched to the size and native diameter of the obstructed segment of the artery to be dilated. If the balloon size and diameter is smaller than the native artery, the results of balloon angioplasty are suboptimal, requiring a second dilation with a larger-sized balloon. In some cases, the result is a failed procedure, which may require either a second separate angioplasty procedure (especially if too much contrast material was already used) or bypass surgery. If the balloon is oversized in relation to the obstructed segment of the native vessel, the inner wall of the artery may dissect from the remainder of the artery and may occlude the vessel completely, causing total cessation of blood flow to the target area of the myocardium. This complication, except in rare occasions, leads to acute myocardial infarction and necessitates emergency bypass surgery. If the acute occlusion leads to a large infarction, death is a possibility.

The most common balloon diameters in demand for coronary angioplasties are 2.0 mm, 2.5 mm, 3.0 mm and 3.5 mm. The 2.0 mm and 2.5 mm balloons are used in patients with small caliber coronary arteries or in the distal coronary branches of patients with otherwise normal-sized coronary arteries. The 3.0 mm and 3.5 mm balloons are generally used in the proximal and larger native coronary arteries. If a patient has a single obstruction in the right or left coronary artery system, a single balloon catheter with a matching diameter and size will be selected for the intended dilation procedure. When the balloon is inflated inside the obstructed segment of the native artery, the balloon should maintain the original preshaped configuration and diameter under the maximum allowed pressure, which is generally up to 150 psi. Polymers such as PVC (polyvinylchloride) and various derivatives of polyethylene have proved to be suitable for making balloon catheters for coronary angioplasty. New polymer derivatives, including variations of Mylar material, are gaining popularity because of their high tensile strength and their potential for making very thin-walled dilation balloons.

In single lesion dilations, the choice of a properly-sized balloon catheter is relatively simple, although there are instances in which the original selection of the balloon catheter is inadequate so that a second balloon Ccatheter is necessary to complete the procedure successfully. However, in multi-vessel disease, balloon catheter selection becomes compounded and complex. For example, a patient may have three lesions in his left coronary artery, and all three lesions may be approachable individually for successful balloon angioplasty. But such lesions may be in vessels of different sizes, such as a 3.0 mm lesion in the proximal portion of the left anterior descending artery (LAD), a 2.0 mm lesion in the distal segment of the LAD, and a 2.5 mm lesion in the superior obtuse marginal artery. With currently available balloon catheters, angioplasty of these three differently-sized lesions is not always impossible, but it is cumbersome and inefficient. For each lesion, a matching balloon catheter is exchanged and manipulated into the target lesion under fluoroscopy with numerous contrast injections. To do this three times in a row requires roughly three times the procedure time, three times the contrast amount, and a minimum of three separate balloon catheters and their accessory devices. In light of the forecast that approximately two thirds of 450,000 to 500,000 patients in the 1990's will need multi-vessel coronary angioplasty, it is clear that there is a need for a major advance in balloon angioplasty that will provide more efficient and cost effective angioplasty balloon systems specifically designed (and suited) for multi-vessel coronary angioplasty.

SUMMARY OF THE INVENTION

The present balloon angioplasty catheter invention is specifically designed for dilation of multiple vessels of different sizes. The present invention also includes a method of using this new catheter in performing multi-vessel angioplasty procedures in a much shorter time and at significantly reduced risk to the patient than is possible with prior art technology.

The catheter of the present invention is a multi-lumen catheter bearing a plurality of individually inflatable and deflatable balloons of predetermined, different sizes. The balloons are coaxial and at least two of the balloons are concentric, i.e., one balloon is inside a larger, separately inflatable balloon.

The present invention is designed for compatibility with existing and commercially available guidewires and guiding catheters, requiring, at most, minimal modification of those existing systems.

The balloons utilized in the present invention must meet stringent requirements that are unique to angioplasty balloons. They are: (a) the balloon must maintain its predetermined precise diameter and its original configuration under high inflation pressures (typically up to 150 psi or more) without significant or undue stretch or deformation; (b) the material used in construction of the balloon must have a high tensile strength and not rupture during inflation to the prescribed high pressure; (c) the balloon must be independently inflatable and deflatable under the external control of the operator; (d) the cross-sectional profile of the balloon should be low (0.035" to 0.065" or less in diameter) when it is deflated with negative pressure so that it can pass through the tight and sometimes very hard internal lumen of the stenotic segment of a target artery; and (e) the material must be flexible as well as resilient so that the balloon catheter can negotiate the tortuous and sometimes irregular artery by following or advancing over a guidewire already placed in the artery ahead of the balloon catheter.

Thus, in accordance with the present invention, there is provided a catheter for performing balloon angioplasty, comprising an elongate, flexible catheter shaft having a plurality of lumens therethrough, a plurality of imperforate angioplasty balloons on the shaft, with the interior of each of the balloons connected to a different lumen for separate inflation and deflation of the balloon. Each of the balloons has a predetermined maximum inflated diameter and is formed of non-elastomeric material. Each balloon is capable of substantially maintaining the predetermined maximum inflated diameter at inflation pressures of up to 100 psi, preferably up to 150 psi, and most preferably up to 200 psi. The balloons on the catheter comprise a first balloon on the catheter shaft near the distal end thereof, and a second balloon on the catheter shaft on top of the first balloon, so that the first balloon is at least partially inside the second balloon, and the maximum inflated diameter of the first balloon is less than the maximum inflated diameter of the second balloon. The first balloon is preferably completely inside the second balloon.

In one embodiment of the present invention, the catheter shaft has a central lumen extending longitudinally therethrough for receiving a steerable guidewire of conventional design. The catheters of the present invention may further comprise a lumen for permitting the flow of blood through the catheter shaft past the balloons. This lumen is preferably the central lumen.

In accordance with another embodiment of the present invention, an axial torque guidewire extends through the catheter shaft and out of the distal end thereof, and the proximal ends of the first balloon and the second balloon are bonded to the distal end of the catheter shaft, and the distal ends of the first balloon and the second balloon are bonded to the guidewire.

In accordance with another aspect of the present invention, a third balloon is provided on the catheter shaft distal of but adjacent to the first balloon and the second balloon. The maximum inflated diameter of the third balloon is smaller than the maximum inflated diameter of the first balloon. Thus, the diameter of the balloons increases from the distal balloon to the proximal balloon and from the inner balloon to the outer balloon. The three-balloon catheter may be provided with an axial torque guidewire extending through the catheter shaft and out of the distal end of the catheter shaft, and the distal end of the third balloon may be bonded to the wire with the proximal end of the third balloon and both proximal and distal ends of the first and second balloons bonded to the catheter shaft.

In accordance with another embodiment of the three-balloon catheter, the catheter extends through the first, second, and third balloons, and a central lumen extends through the catheter shaft for receiving a steerable guidewire. Holes may be provided in communication with a lumen, preferably the central lumen, for permitting the flow of blood through the catheter shaft past the balloons.

In one emobidment of the three-balloon catheter, an attachment site is provided on the catheter shaft to which the proximal end of the third balloon and the distal end of the second balloon are joined, wherein either the second balloon or the third balloon has been formed to at least partially prolapse over the attachment site. The prolapsed balloon is preferably the distal, third balloon, and it preferably prolapses over substantially the entire attachment site. The third balloon may be permanently formed into the prolapsed shape, and also may be bonded to the attachment site to hold it into the prolapsed shape.

In one embodiment of the invention, two of the balloons are formed from the same piece of material with a narrow waist connecting them. This narrow waist of balloon material is attached to the central attachment site.

In another embodiment of the three-balloon catheter, the distal end of the second balloon is attached to the central attachment site on the catheter shaft, and the proximal end of the third balloon is attached to the wall of the second balloon proximally of the central attachment site on the catheter shaft so that the central attachment site is inside the third balloon. Steerable guidewires, bypass sideholes, or axial torque guidewires may be provided in any of these three balloon designs.

In yet another embodiment of the present invention, the three-balloon catheter further includes a fourth balloon on top of the third balloon, so that the third balloon is at least partially inside the fourth balloon, wherein the maximum inflated diameter of the fourth balloon is greater than the maximum inflated diameter of the third balloon, but less than the maximum inflated diameter of the first balloon. Thus, in this design, the first balloon is mounted inside the second balloon, the third balloon is mounted distal of the first and second balloons, and the fourth balloon is mounted on top of the third balloon. The catheter shaft may pass entirely through all four balloons, and may be provided with a means for permitting blood flow through the catheter shaft to bypass the balloons. Alternatively, the catheter shaft may have its distal end at the attachment site between the two sets of balloons, and an axial torque guidewire may extend through the catheter shaft, out of the distal end thereof, and through the third and fourth balloons. The distal ends of the third and fourth balloons may then be bonded directly to the axial torque guidewire.

In the four-balloon design, the proximal end of the fourth balloon may be attached to the wall of the second balloon proximally of the point on the catheter shaft to which the distal end of the second ballon is attached.

In another embodiment of the four-balloon catheter, the first and second balloons may be concentric, the third balloon may be attached to the catheter shaft distally of the first and second balloons, and a fourth balloon may be attached to the catheter distally of the third balloon. The third and fourth balloons may have both ends attached to the catheter shaft, or the proximal end of the third balloon may be attached to the distal wall of the second balloon and the proximal end of the fourth balloon may be attached to the distal wall of the third balloon. The distal end of the fourth balloon may, alternatively, be attached to an axial torque guidewire.

A concentric three balloon catheter in accordance with yet another aspect of the present invention may comprise a first balloon on the catheter shaft, a second balloon over the first balloon, and a third balloon over the second balloon, so that all three balloons are concentric and coaxial. The maximum inflated diameter of the first balloon is less than that of the second balloon, which in turn is less than that of the third balloon. The catheter shaft may terminate inside the three balloons, with an axial torque guidewire extending through the catheter shaft and out of the distal end of the three balloons, with the distal ends of each of the three balloons being bonded to the axial torque guidewire. Alternatively, the catheter shaft may extend completely through all three balloons, so that both ends of each of the three balloons are bonded to the catheter shaft. A central lumen may be provided in the catheter shaft for receiving a steerable guidewire.

In all of the embodiments of the present invention, radiopaque markers may be provided on the catheter to mark the longitudinal location of any or all of the balloons on the catheter.

For coronary angioplasty, it is preferred that none of the balloons exceed about 40 mm in length, and most preferably none of the balloons exceed about 30 mm in length. For peripheral angioplasty, it is preferred that none of the balloons exceed about 100 mm in length, and they most preferably do not exceed about 80 mm in length. For coronary angioplasty, it is preferred that the maximum inflated diameter of each of the balloons does not exceed about 4.5 mm. For peripheral angioplasty, it is preferred that the maximum inflated diameter of each of the balloons does not exceed about 15 mm.

Also provided in accordance with the present invention is a surgical procedure for performing vascular balloon angioplasty, comprising the steps of selecting an angioplasty catheter having thereon a first balloon with a first predetermined maximum inflated diameter and a second balloon with a different second maximum inflated diameter, positioning the first balloon inside a first stenosis in a blood vessel and and inflating the first balloon to dilate the first stenosis, and positioning the second balloon inside a second stenosis in a blood vessel and inflating the second balloon to dilate the second stenosis. The first balloon should be deflated after dilating the first stenosis and before dilating the second stenosis, so that only one balloon is inflated at a time. The procedure is preferably performed on atherosclerotic stenoses.

The predetermined maximum inflated diameter of the first balloon is preferably approximately equal to the diameter of the native vessel in which the first stenosis is located, and the predetermined maximum inflated diameter of the second balloon is preferably approximately equal to the diameter of the native vessel in which the second stenosis is located. The vessels in which the procedure of the present invention is performed may be coronary arteries.

In accordance with another aspect of this invention, the angioplasty catheter has a third balloon thereon, wherein the third balloon has a maximum inflated diameter different from that of the first balloon and the second balloon, and the method further comprises the steps of positioning the third balloon inside a third stenosis in a blood vessel, and inflating the third balloon to dilate the third stenosis. The third stenosis may advantageously be an atherosclerotic stenosis, and the predetermined maximum inflated diameter of the third balloon is preferably approximately equal to the diameter of the native vessel in which the third stenosis is located.

In accordance with yet another aspect of the surgical procedure of the present invention, there is provided a method for performing balloon angioplasty comprising the steps of selecting an angioplasty catheter having a first balloon with a first predetermined maximum inflated diameter and a second balloon having a different, larger predetermined maximum inflated diameter than the first balloon, wherein the first balloon is located on the catheter distally of the second balloon, positioning the first balloon inside a stenosis inside a blood vessel, inflating the first balloon to dilate the stenosis, deflating the first balloon, advancing the second balloon into the partially dilated stenosis, and inflating the second balloon with the first balloon deflated to further dilate the stenosis. It is preferred that the maximum inflated diameter of the second balloon is approximately equal to the diameter of the native vessel in which the stenosis is located. The vessels may advantageously be coronary arteries.

BRIEF DESCRIPTION OF THE DRAWINGS

FIG. 1 is a perspective view of the distal end of a three-balloon catheter of the present invention, in which the balloons are shown partially cut away.

FIG. 2 is a cross-section of the catheter of FIG. 1, taken along the line 2—2.

FIG. 3 is a cross-section of the catheter of FIG. 1, taken along the line 3—3.

FIG. 4 is a cross-section of the catheter of FIG. 1, taken along the line 4—4.

FIG. 5 is a cross-section of the catheter of FIG. 1, taken along the line 5—5.

FIG. 6 is a schematic representation of a concentric double balloon catheter for use with a steerable guidewire.

FIG. 7 is a schematic representation of a concentric double balloon catheter with an axial torque guidewire.

FIG. 8 is a schematic representation of a concentric triple balloon catheter for use with a steerable guidewire.

FIG. 9 is a detailed view of the central attachment site in FIG. 8, showing the balloons in cross-section.

FIG. 10 is a schematic representation of a concentric triple balloon catheter with an axial torque guidewire.

FIG. 11 is a schematic representation of a concentric triple balloon catheter in which the distal balloon is prolapsed, for use with a steerable guidewire.

FIG. 12 is a close-up view of the central attachment site in FIG. 11, with the balloons in cross-section, illustrating the prolapsed bonding joint.

FIG. 13 is a schematic representation of a concentric triple balloon catheter with prolapse bonding and an axial torque guidewire.

FIG. 14 is a schematic representation of a concentric triple balloon catheter with overlap bonding between the outer balloon and the distal balloon for use with a steerable guidewire.

FIG. 15 is a close-up view of the method of making the overlap joint in FIG. 14, showing the balloons and a die in cross-section.

FIG. 16 is a schematic representation of a concentric triple balloon catheter utilizing overlap bonding and having an axial torque guidewire.

FIG. 17 is a schematic representation of a quadruple balloon catheter having two pairs of concentric balloons in tandem for use with a steerable guidewire.

FIG. 20 is a schematic representation of a quadruple balloon catheter of the type shown in FIG. 19, with an axial torque guidewire.

FIG. 21 is a schematic representation of a triple concentric balloon catheter for use with a steerable guidewire.

DETAILED DESCRIPTION OF THE INVENTION

I. Catheter Design

Figure 18:
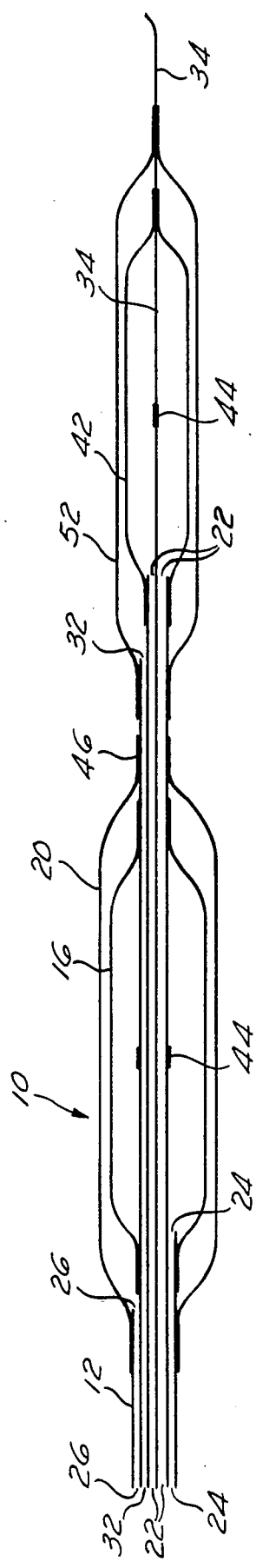
FIG. 18 is a schematic representation of a quadruple balloon catheter having two pairs of concentric balloons mounted in tandem having an axial torque guidewire.

The catheters of the present invention may be fabricated from conventional commercially available polymers, but may also utilize improved materials in the future as they become available. The balloon segments of the present invention may be shaped or blown using well known hot water bath, heat torch, or thermal oven methods. The balloon joint bonding processes that may be used include heat bonding, vulcanization bonding, solvent bonding, ultrasonic welding, laser welding, and glue bonding.

In order to achieve the objectives of the present invention, a number of different embodiments of the angioplasty balloon catheter have been provided. These different balloon models can be classified according to the architectural embodiment and can be subclassified according to their functional characteristics and according to the fabrication techniques used, and especially balloon attachment techniques and balloon geometry.

The following is a summary of different embodiments and permutations of the present invention:

(1) Models of Balloon Design
    (a) Concentric Double Balloons
    (b) Concentric Triple Balloons
    (c) Concentric Quadruple Balloons
    (d) Mixed Quadruple Balloons (2) Functional Types of Balloon Catheters
    (a) Steerable Guidewire type
    (b) Axial Torque type
    (c) Bypass Sidehole type (3) Variations of Balloon Joint Bonding
    (a) Separate tandem bonding
    (b) Contiguous tandem bonding
    (c) Prolapse tandem bonding
    (d) Overlap Tandem bonding Many features common to all the balloon designs of the present invention are illustrated in FIG. 1. In that figure, the catheter 10 of the present invention is provided with a catheter shaft 12 having a distal end 14 and a proximal end (not shown) opposite the distal end.

A first balloon 16 is provided near the distal end 14 of the catheter shaft 12. The first balloon 16 may be formed of polyvinylchloride, polyethylene, Mylar brand polyester material (made by duPont), or other suitable film-forming material capable of withstanding pressures of 100 psi, preferably 150 psi or 200 psi, without bursting or significantly stretching, when formed into a thin-walled angioplasty balloon. Mylar is particularly preferred. Generally, the thickness of the wall 17 of the balloons will be between about 0.01 mm and 0.10 mm. This thickness is greatly exaggerated in the Figures for purposes of illustration only. The balloon 16 may be attached to the catheter shaft 12 using any of the well known connection techniques, including solvent bonding, adhesive bonding, heat-shrink bonding, thermal welding and so on. The first balloon 16 is preferably heat formed or blown to the desired shape and configuration prior to attachment to the catheter shaft 12. The first balloon is preferably generally cylindrical, and may be tapered at the proximal and distal ends.

A second balloon 20 is provided on the catheter shaft 12 on top of the first balloon 16 so that the first balloon 16 is at least partially inside the second balloon 20. As illustrated in FIG. 1, the first balloon 16 is preferably completely inside the second balloon 20.

The catheter shaft 12 is provided with a central lumen 22, a first lumen 24, and a second lumen 26. The central lumen 22 extends longitudinally through the catheter shaft 12 and terminates at the distal end 14 of the catheter 10. The first lumen 24 extends through the catheter shaft 12 and terminates inside the first balloon 16, permitting the first balloon 16 to be individually inflated and deflated by the introduction of and removal of fluid through the first lumen 24 as indicated by the arrow 25. Similarly, the second lumen 26 terminates inside the second balloon 20, permitting the second balloon 20 to be separately inflated and deflated by introduction of and removal of fluid through the second lumen 26 as indicated by the arrows 27. The spatial arrangement of the two balloons 16, 20 is concentric and symmetrical.

A third balloon 42 is provided adjacent to the distal end 14 of the catheter shaft 12 and adjacent to the distal ends of the first balloon 16 and the second balloon 20. The third balloon is constructed of substantially the same material in substantially the same manner as the first balloon 16 and the second balloon 20. A third lumen 28 is provided in the catheter shaft 12 in fluid communication with the interior of the third balloon 42, thereby permitting the third balloon 42 to be inflated and deflated by introducing fluid into and removing fluid from the interior of the third balloon 42 via the third lumen 28 as indicated by arrow 29.

Radiopaque markers 44 are provided inside each of the balloons on the catheter shaft 12. These radiopaque markers, which may advantageously be made of metal or other radiopaque material, are preferably longitudinally located on the catheter shaft in the center of each of the balloons 16, 20, 42. In this way, the exact placement of the balloons can be ascertained through fluoroscopy.

The catheter shaft may be constructed in any desired way to provide the requisite number of lumens terminating inside the desired balloons. The catheter 10 is shown in several cross sections in FIGS. 2, 3, 4, and 5. In FIG. 2, a cross section of the catheter shaft 12 alone which is taken proximally of all of the balloons 16, 20, 42, it can be seen that the catheter shaft 12 (which may be made of any suitable medical plastic) has a first lumen 24, a second lumen 26, a third lumen 28, and a central lumen 22 running therethrough. Note that, while the central lumen 22 is larger than the numbered lumens 24, 26, 28, the central lumen need not be actually centrally located in the catheter shaft 12.

With reference now to FIG. 3, this is a cross-section of the catheter 10 through the second balloon 20 at the point where the proximal end of the first balloon 16 is attached to the catheter shaft 12. The cross-section is taken along the line 3—3. Note that the catheter shaft 12 now has a central lumen 22, a first lumen 24, and a third lumen 28. There is no longer any second lumen 26, this lumen having terminated inside the second balloon 20 proximally of the first balloon 16. The proximal end of the first balloon 16 in FIG. 3 is bonded tightly to the catheter shaft 12. The second balloon 20 is shown fully inflated, although it will, of course, ordinarily be deflated and collapsed against the catheter shaft 12.

FIG. 4 illustrates the balloon construction in a cross-section taken along the line 4—4 through the first balloon 16 and the second balloon 20. Note that the catheter shaft 12 now has only the central lumen 22 and the third lumen 28, the first lumen 24 having terminated inside the first balloon 16. The first balloon 16 and the second balloon 20 are coaxial and concentrically surround the catheter shaft 12. In FIG. 4, the first balloon 16 and the second balloon 20 are illustrated in fully inflated form. However, both balloons 16, 20 will ordinarily be fully deflated and collapsed against the catheter shaft 12.

FIG. 5 is a cross-section taken along the line 5—5 through the third balloon 42. Note that the catheter shaft 12 now has only a single lumen, the central lumen 22 through which a steerable guidewire may be inserter. The third balloon 42 surrounds the catheter shaft 12 concentrically and, like the other balloons 16, 20, is coaxial with the catheter shaft 12.

Several specific embodiments of the balloon catheter 10 of the present invention will be described hereinafter in greater detail in connection with schematic drawings of the catheter construction. To the extent that the components and features of the catheters in the various embodiments of the present invention correspond, they will retain the same reference numerals from Figure to Figure and will not be separately explained.

In the following discussions, balloon models, functional types, and bonding joints will be detailed according to the balloon classifications of these inventions. The embodiment and the fabrication sequences will also be described.

A. Concentric Double Balloons (1) Steerable Guidewire Type

This design has two balloons of different diameter constructed on a single shaft in a concentric manner so that the smaller balloon is arranged inside the larger balloon. Each balloon is independently inflatable and deflatable so that this single catheter is capable of dilating two different lesions of two different diameters in the same patient. The inner balloon has smaller diameter and length than the outer balloon.

With reference now to FIG. 6, a concentric double balloon catheter is illustrated. The catheter 10 has a catheter shaft 12 on which are mounted a first balloon 16 and a second balloon 20. The first balloon 16 is smaller than the second balloon 20 in diameter, and is located at least partially inside the second balloon 20, preferably completely inside the second balloon 20.

The catheter shaft 12 is provided with multiple longitudinal lumens or passageways therethrough. These lumens are schematically illustrated in FIG. 6 as two-dimensional paths between solid lines. Thus, on the proximal side of the balloons 16, 20, the catheter shaft 12 includes three lumens. Because the catheter shaft 12 is shown schematically in two dimensions in FIG. 6, it is not representative of the actual three-dimensional arrangement of the lumens in the catheter shaft 12. Moreover, the actual three-dimensional arrangement of the lumens in the shaft is not particularly critical.

A typical catheter 10 could have an inner first balloon 16 that is 2.0 mm in diameter and 15 mm in length, and an outer second balloon 20 that is 2.5 mm in diameter and 20 mm in length. However, the balloons 16, 20 can be made in any variation and combination of sizes, with balloon diameters for coronary angioplasty of from about 1.0 mm to about 5.0 mm and lengths of from about 7 mm to about 40 mm, respectively. Thus, the diameter of the first balloon 16 may be 1.0 mm, 1.5 mm, 2.0 mm, 2.5 mm, 3.0 mm or 3.5 mm, and the diameter of the outer second balloon 20 may be 1.5 mm, 2.0 mm, 2.5 mm, 3.0 mm, 3.5 mm, 4.0 mm, 4.5 mm, or 5.0 mm (provided that the second balloon 20 is larger than the first balloon 16). Similarly, the length of the first balloon 16 may be 7 mm, 10 mm, 12 mm, 15 mm, 20 mm, 25 mm, or 30 mm, and the length of the outer balloon may be 10 mm, 12 mm, 15 mm, 20 mm, 25 mm, 30 mm, 35 mm, or 40 mm, provided that the second balloon 20 is longer than the inner balloon.

The fabrication method for the balloons may be the same as the conventional currently-available fabrication techniques for single balloon catheters. See, e.g., U.S. Pat. Nos. 4,195,637 and 4,323,071. The second balloon 20 can be blown separately and then laid coaxially over the already finished first balloon 16 before the two ends of the second balloon 20 are bonded to the catheter shaft 12 as shown in FIG. 6. The central lumen 22 of the balloon catheter 10 preferably has an inner diameter of 0.016" to 0.018", just large enough to accommodate a 0.014" conventional steerable guidewire inside and to monitor the distal pressure. The outer diamter of the proximal shaft 12 should be size French 4.5 or less.

(2) Bypass Sidehole Type

In one preferred embodiment of the present invention, the catheter shaft 12 is provided with proximal holes 36 on the proximal side of the balloons 16, 20 and distal holes 40 on the distal side of the balloons 16, 20. These holes 36, 40 are shown schematically in FIG. 6 and communicate with a lumen that is not used for inflating or deflating the balloons 16, 20. Although a special lumen may be provided, the holes 36, 40 preferably are connected only to the central lumen 22 and do not interrupt any other lumen. Thus, these holes provide a means for permitting the flow of blood through the catheter shaft past the balloons 16, 20. The provision of holes 36, 40 to permit blood to bypass the balloons is important in angioplasty procedures in which it is desirable to prevent occlusion of the blood vessel during the positioning, inflation, deflation, and removal of the balloons. Thus, even when one of the balloons 16, 20 is inflated, occluding the vessel, blood can flow through the proximal holes 36, through the central lumen 22, and out of the distal holes 40 and the distal end of the central lumen 22. Because of the holes 36, 40, distal pressure monitoring through the central lumen is not possible, although a separate lumen could be provided for that purpose. Nevertheless, a conventional steerable guidewire may be used with the bypass sidehole type catheter.

It is preferred that the proximal holes 36 are located within about 1" of the proximal end of the second balloon 20. Three to five proximal holes may advantageously be used. The distal holes 40 may advantageously be located between the distal end 14 of the catheter 10 and the distal joint where the second balloon 20 is joined to the catheter shaft 12. Two distal holes 40 will ordinarily be sufficient because blood can also flow out of the distal end of the central lumen 22.

(3) Axial Torque Type

The axial torque type of concentric double balloon illustrated in FIG. 7 has a significantly different catheter shaft design and torque control mechanism than the catheter illustrated in FIG. 6. However, the concentric arrangement of the balloons is the same as the design previously discussed.

This embodiment of the present invention may be made with as few as two lumens in the catheter shaft 12. As indicated in FIG. 7, the central lumen 22 is directly connected to the first balloon 16. There is a tapered guidewire 34 with a diameter of 0.008" to 0.016" running from the proximal end of the catheter 10 to the distal end 14 of the of catheter 10 for torque control of the distal tip of the guidewire 34. Both the inner and outer balloons 16, 20 preferably have their distal joints directly bonded to the guidewire 34. The distal end 14 of the catheter 10 beyond the distal joint of the second balloon 20 comprises an extending portion of the flexible guidewire 34 about 1.5 to 2.5 cm in length.

The advantage of the balloon having the axial torque guidewire is the ability to provide a catheter with an extremely low profile, because the collapsed balloons are not filled with the catheter shaft 12 and, thus, can collapse to the fullest possible degree.

B. Concentric Triple Balloons/Tandem Bonding

In one preferred embodiment of the invention, three balloons, each of which is separately inflatable and deflatable, are provided on the catheter shaft. It is preferred that a single, distal balloon be provided, and that there be a pair of concentric balloons directly adjacent to the distal balloon. The distal balloon and the concentric balloons are mounted in tandem on the catheter shaft, that is, one next to the other. Various preferred embodiments of the concentric triple balloon having a tandem arrangement are discussed in more detail below.

(1) Steerable Guidewire Type

As illustrated in FIG. 8, a first balloon 16 and a second balloon 20 are concentrically mounted on the catheter shaft 12, with the first balloon 16 inside of the second balloon 20. The first balloon 16 has a smaller diameter than the second balloon 20. A third balloon 42 is mounted on the catheter shaft 12 distally of the first and second balloons 16, 20. Each of the balloons 16, 20, and 42 have a different diameter, and the third balloon 42, which is the distal balloon, is preferably smaller than the first balloon 16. This arrangement is advantageous because the smaller, distal balloon 42, in its collapsed state, can penetrate and, if necessary, partially dilate constricted portions of vessels, thus making room for the collapsed concentric first and second balloons 16, 20 to penetrate the constricted area. In one typical embodiment, the distal third balloon 42 is about 2.0 mm in diameter and about 15 mm in length, the inner first balloon 16 is about 2.5 mm in diameter and about 15 mm in length, and the outer second balloon 20 is about 3.0 mm in diameter and about 20 mm in length. The diameter and length of these three balloons can, of course, be varied to satisfy any particular clinical and/or market need. The incremental diameter of the balloons 16, 20, 42 may be between about 1.0 mm and about 4.5 mm and the length of the balloons may be anywhere from about 7 mm to about 40 mm. These sizes are particularly suited for coronary angioplasty procedures. The same design, with larger balloons, may be used for peripheral angioplasty procedures.

If desired, each of the balloons 16, 20, 42, may be separately fabricated and attached to the catheter shaft 12. Mounting separate balloons one next to the other is referred to as "separate tandem" mounting. However, in a preferred embodiment, as illustrated in FIG. 9, two of the balloons are blown from a single tapered tube with a narrow waist 45 in between the two balloons. This is referred to as "contiguous tandem" mounting. These balloons are preferably the first balloon 16 and the third balloon 42. This single unit of two balloons is mounted on the catheter shaft 12 with the smallest balloon of the two at the distal tip. These two balloons are then bonded to the shaft in alignment with the appropriate lumen openings. The narrow waist 45 is bonded to a central attachment site 46 on the catheter shaft 12. Once the first balloon 16 and the third balloon 42 (whether or not formed from a single unitary tube of balloon material) have been bonded to the catheter shaft 12, the second balloon 20 may be placed over the first balloon 16 and bonded into place. Radiopaque markers 44 may be provided centrally beneath the balloons on the catheter shaft 12 to indicate the longitudinal location of the balloons 16, 20, 42 on the catheter shaft 12.

A first lumen 24 is provided through the catheter shaft 12. This lumen terminates inside the first balloon 16 and permits inflation and deflation of the first balloon 16 by introduction and removal of a fluid through the first lumen 24 into and out of the first balloon 16. A second lumen 26 is provided in the catheter shaft 12 in the same way as the first lumen 24, providing a fluid passageway through the catheter shaft 12 and into the second balloon 20 so that the second balloon 20 can be inflated and deflated by introducing a fluid through the second lumen 26.

Similarly, a third lumen 28 is provided through the catheter shaft 12, terminating in the third balloon 42 to permit inflation and deflation of that balloon 42.

In the embodiment of the coaxial triple balloon illustrated in FIG. 8, a central lumen 22 also is provided. The dimensions of the central lumen are sufficient to accommodate a 0.014 inch steerable guidewire and, at the same time, to permit monitoring of the distal pressure through the central lumen 22.

The outside diameter of the catheter shaft 12 should not be larger than about size French 4.5 or 4.7.

(2) Bypass Sidehole

In one preferred embodiment of the design illustrated in FIG. 8, the catheter may be provided with proximal holes 36 on the proximal side of the second balloon 20 and with distal holes 40 on the distal side of the third balloon 42. As discussed in connection with the coaxial double balloon catheter illustrated in FIG. 6, these holes 36, 40 permit blood to bypass the balloons 16, 20, 42 through the central lumen 22 to perfuse the distal myocardial segment.

(3) Axial Torque Type

A different embodiment of the concentric triple balloon is illustrated in FIG. 10. As with the design in FIG. 8, this design has a first balloon 16 inside of a larger, second balloon 20, with a distally-located third balloon 42. At least one end of each balloon 16, 20, 42, is mounted on the catheter shaft 12. However, in this design, the central lumen 22 is directly connected to the third balloon 42, for inflating and deflating the third balloon 42. There is a tapered steel axial torque guidewire 34 with a diameter of 0.016 inches to 0.008 inches running from the proximal end of the catheter 10 to the distal end 14 of the catheter 10 for torque control of the distal tip of the guidewire 34. Although both the proximal ends and the distal ends of the first and second balloons 16, 20 are bonded to the catheter shaft 12, as is the proximal end of the third balloon 42, the distal end of the third balloon 42 is bonded directly to the axial torque guidewire 34. One of the radiopaque markers 44 is placed on the catheter shaft 12 in the center of the first and second balloons 16, 20, and the other radiopaque marker 44 is centrally located inside the third balloon 42 on the steerable guidewire 34.

C. Concentric Triple Balloons/Prolapse Tandem (1) Steerable Guidewire Type

In accordance with one advantageous embodiment of the coaxial triple tandem balloon design, the effective length of the catheter occupied by the three balloons may be shortened by prolapsing one of the balloons, as illustrated in FIG. 11. In this design, the first balloon 16 and the second balloon 20 are mounted on the catheter shaft in the same way as described in connection with FIGS. 6 and 8. The distal end of the second balloon 20 and the proximal end of the third balloon 42 are attached to the catheter shaft 12 at a point denominated as the central attachment site 46. The proximal end of the third balloon 42 is then folded proximally (prolapsed) back over at least a portion of the central attachment site 46, as is shown in more detail in FIG. 12. It is preferred that the third balloon is prolapsed over substantially all of the central attachment site 46 so that the prolapsed portion 47 is directly adjacent to the second balloon 20. This prolapse design permits the elimination of the "dead space" of the central attachment site, providing a shorter, more easily manipulated balloon portion of the catheter 10. This shortened arrangement is advantageous in negotiating tight turns during the insertion and positioning of the catheter. The prolapsed portion 47 is a part of the inflatable portion of the third balloon 42 and is located over the central attachment site 46 and over the point where the proximal end of the third balloon 42 is connected to the catheter shaft 12.

One suitable fabrication technique for the prolapse design is to bond the first and second balloons 16, 20 to the catheter shaft 12 as previously described, to bond the proximal end of the third balloon 42 to the catheter shaft 12 at the central attachment site 46 and to then prolapse the third balloon into the desired position. The second balloon 20 and the third balloon 42 are then inflated with positive pressure (e.g., 100–120 psi), and the prolapsed portion 47 of the third balloon 42 in contact with the central attachment site and, optimally, in contact with the second balloon 20, is bonded thereto with an adhesive 48 or with solvent welding. This bonding technique insures that the third balloon 42 maintains its prolapsed position and will prevent forward and backward "rolling" movement during catheter movements and balloon inflation.

In this prolapsed embodiment of the invention, it is preferable to form each of the three balloons from separate pieces of material, in order to avoid an extra layer under the prolapsed third balloon in the central attachment site.

(2) Bypass Sidehole Type

In one preferred embodiment of the catheter illustrated in FIG. 11, proximal holes 36 and distal holes 40 are provided in the catheter shaft 12 in communication with the central lumen 22 in the same manner and for the same reasons as discussed previously.

(3) Axial Torque Type

A coaxial triple balloon catheter of the axial torque type featuring a prolapsed bonding arrangement is illustrated in FIG. 13. The catheter of FIG. 13 corresponds to the catheter of FIG. 10, except that the third balloon 42 is prolapsed over the central attachment site 46 in the same way as described in connection with FIG. 11.

D. Concentric Triple Balloon/Overlap-Proximal (1) Steerable Guidewire Type

An alternative to the use of a prolapsed third balloon 42 to cover the central attachment site 46 is disclosed in FIG. 14. In this design, the first balloon 16 and the second balloon 20 are attached to the catheter shaft 12 in the same manner as disclosed in connection with FIGS. 6, 8, and 11. The distal end of the second balloon 20 is connected to the catheter shaft 12 at the central attachment site 46. A central lumen 22 extends the length of the catheter shaft 12 and through all three balloons 16, 20, 42. The central lumen 22 is of sufficient dimension to accommodate a steerable guidewire. A first lumen 24 in the catheter shaft 12 is in fluid connection with the interior of the first balloon 16, a second lumen 26 in the catheter shaft 12 terminates inside the second balloon 20, and a third lumen 28 in the catheter shaft 12 is in fluid connection with the interior of the third balloon 42.

In the catheter illustrated in FIG. 14, overlap bonding of the third balloon 42 and the second balloon 20 is utilized to eliminate the gap between the second balloon 20 and the third balloon 42. This is shown more clearly in FIG. 15. The second balloon 20, at its distal end, preferably has a tapered portion 50 where the second balloon 20 tapers down from its maximum inflated diameter to the diameter of the shaft 12. The proximal end of the third balloon 42 is bonded, not to the catheter shaft 12, but to the tapered portion 50 of the second balloon 20. In order to maintain an ideal profile for the second and third balloons 20, 42, when inflated, it is preferred that the inflated diameters of the proximal end of the third balloon 42 and the part of the tapered portion 50 of the second balloon 20 to which it is bonded be substantially the same. Of course, the same result can be achieved by bonding the distal end of the second balloon 20 to the wall of the proximal end of the third balloon 42 distally of the central attachment site 46.

The fabrication method for forming the overlap joint between the third balloon 42 and the tapered portion 50 of the second balloon 20 may be any suitable technique, such as solvent bonding, adhesive bonding, vulcanization, or ultrasonic welding. In order to create the overlap balloon joint, the proximal end of the third balloon 42 which is to be bonded to the tapered portion 50 of the second balloon 20 preferably has a flared end 51 to fit the taper of the tapered portion 50. Once the third balloon 42 has been properly placed on the tapered portion 50 of the second balloon 20, and adhesive 48 or solvent has been applied to the joint, the catheter is preferably inserted into a die 53 having a cavity 54 that matches the contours of the inflated third balloon 42 and the inflated second balloon 20. The second balloon may then be fully inflated inside the die, pressing the overlap joint on the tapered portion 50 against the inside of the die until the joint has cured.

(2) Bypass Sidehole Type

As in FIGS. 6, 8, and 11, proximal holes 36 on the proximal side of the second balloon 20 and distal holes 40 on the distal side of the third balloon 42 may be provided to permit blood flow through the holes 36, 40, and the central lumen 22 during balloon inflation in the coronary artery.

(3) Axial Torque Type

The catheter illustrated in FIG. 16 is an axial torque type of concentric triple balloon catheter utilizing overlap bonding between the second balloon 20 and the third balloon 42 as discussed in connection with FIG. 14. However, the central lumen 22 terminates inside the third balloon 42 and the third balloon 42 is bonded to an axial torque guidewire as discussed in connection with FIGS. 7, 10, and 13.

E. Concentric Quadruple Balloon Catheter

In accordance with yet another embodiment of the present invention, there is provided a concentric quadruple balloon catheter constructed by placing two pairs of concentric balloon in tandem on the catheter shaft. The two distal coaxial balloons are smaller than the two proximal coaxial balloons and the inside balloons are smaller than the outside balloons. Each of the four balloons has a different maximum inflated diameter. Thus, the third balloon 42 is smaller than the fourth balloon 52, and the first balloon 16 is larger than the fourth balloon 52. Each of the four balloons can be inflated and deflated independently. This catheter may be used in coronary angioplasty in a limited number of cases if an extremely thin polymer material is used to construct the balloons. However, typically, these concentric quadruple balloon catheters would be more suited for peripheral vascular angioplasty and valve angioplasty.

(1) Steerable Guidewire Type

A concentric quadruple balloon catheter of the steerable guidewire type is illustrated in FIG. 17. In this design, a first balloon 16 is mounted on the catheter shaft 12 inside of a second balloon 20, and a third balloon 42 is mounted on the catheter shaft 12 distally of the second balloon 20 in substantially the same manner as discussed in connection with FIG. 8. As in FIG. 8, a central lumen 22 extends the length of the catheter shaft 12, and first, second, and third lumens 24, 26, 28, are provided in the catheter shaft in fluid communication with the interiors of the first, second, and third balloons 16, 20, 42, respectively. A fourth balloon 52 is mounted on top of and concentric with the third balloon 42. In addition, a fourth lumen 32 is provided in the catheter shaft 12 in fluid communication with the fourth balloon 52 to provide for separate inflation and deflation of the fourth balloon 52 by introducing a fluid into and removing fluid from the fourth balloon 52 through the catheter shaft 12 via the fourth lumen 32.

For use in peripheral angioplasty, the balloons of the concentric quadruple balloon catheter may advantageously be made in diameters between about 3.0 mm and 10.0 mm. Similarly, the length of the four balloons may advantageously be between 25 mm and 60 mm. It is anticipated that a typical concentric quadruple balloon catheter would have balloons with diameters of 3.0 mm, 4.0 mm, 5.0 mm, and 6.0 mm, having lengths, respectively, of 35 mm, 40 mm, 35 mm, and 40 mm. The central lumen 22 may be used for guidewire insertion during peripheral catheterization. The central lumen bore is preferably made large enough to accommodate a 0.036 inch guidewire in catheters made for peripheral and valve angioplasty.

(2) Bypass Sidehole Type

As in FIGS. 6, 8, 11, and 14, proximal holes 36 and distal holes 40 may be provided on the catheter shaft 12 in fluid communication with the central lumen 22 to permit blood flow through the central lumen 22 past the balloons 16, 20, 42, 52.

(3) Axial Torque Type

A concentric axial torque guidewire version of the quadruple balloon catheter of FIG. 17 is illustrated in FIG. 18. In this design, the first and second balloons 16, 20 and the proximal ends of the third and fourth balloons 42, 52 are bonded to the catheter shaft 12 as in FIG. 17. However, an axial torque guidewire 34 is provided in the central lumen 22, as in FIGS. 7, 10, 13, and 16, and the distal ends of the third and fourth balloons 42, 52 are bonded directly to the guidewire 34. Moreover, while the first, second, and fourth lumens 24, 26, and 32 communicate, respectively, with the first, second, and fourth balloons 16, 20, 52, the central lumen 22 is in fluid communication with the interior of the third balloon 42, so that the catheter shaft 12 may be formed with only four lumens. The axial torque concentric quadruple balloon catheter illustrated in FIG. 18 is potentially usable for coronary angioplasty, and balloons of suitable size may be provided on the catheter. In one preferred embodiment, the balloon diameters, from smallest to largest, may be 2.0 mm, 2.5 mm, 3.0 mm, and 3.5 mm, the lengths of the inner balloons could be 15 mm, and the lengths of the outer balloons could be 20 mm.

F. Mixed Quadruple Balloons

Figure 19:
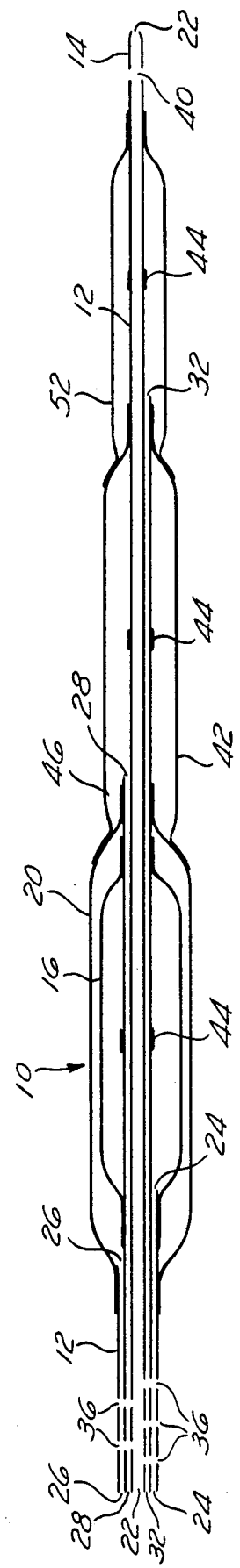
FIG. 19 is a schematic representation of a quadruple balloon catheter having two concentric balloons proximally of two tandem balloons for use with a steerable guidewire.

As illustrated in FIG. 19, the design of the concentric triple balloon catheter of FIGS. 8, 11, and 14, may be modified to provide a fourth balloon 52 located distally of the third balloon 42 on the catheter shaft 12. Although overlap bonding is illustrated in FIG. 19, prolapse bonding as shown in FIG. 12 may also be used. A fourth lumen 32 is provided in fluid communication with the interior of the fourth balloon 52 so that the fourth balloon 52 may be separately inflated and deflated by introducing fluid into and removing fluid from the proximal end of the fourth lumen 32. It is preferred that the fourth balloon 52 be the smallest balloon, that the third balloon 42 be larger than the fourth balloon 52, that the first balloon 16 be larger than the third balloon 42, and that the second balloon 20 be the largest of the four balloons. The steerable guidewire type quadruple balloon catheter illustrated in FIG. 19, because of its diameter and length, is most suited for peripheral angioplasty, and balloon dimensions can be selected accordingly. Balloon diameters may range up to about 10 mm, and balloon lengths may range up to about 60 mm. It is expected, however, that advances in materials science and particularly in balloon material may permit this design to be fabricated in a size suitable for coronary angioplasty. As in FIG. 17, proximal holes 36 on the proximal side of the second balloon 20 and distal holes 40 on the distal side of the fourth balloon 52 may be provided on the catheter shaft 12 in connection with the central lumen 22 to permit blood flow through the central lumen 22 to bypass the balloons 16, 20, 42, 52.

The balloon configuration of FIG. 19 may similarly be applied to make an axial torque mixed quadruple balloon catheter as illustrated in FIG. 20. In this design, the first, second, and third balloons 16, 20, 42, are bonded to the catheter shaft 12, and the proximal end of the fourth balloon 52 is bonded to the wall of the third balloon 42 at a point proximal to where the distal end of the third balloon 42 is bonded to the catheter shaft 12. Unlike the design in FIG. 19, however, the distal end of the fourth balloon 52 is bonded directly to an axial torque guidewire 34. First, second, and third lumens 24, 26, 28 are provided in fluid communication with the interiors of the first, second, and third balloons 16, 20, 42, respectively, and the central lumen 22, through which the axial torque guidewire 34 passes, is in fluid connection with the interior of the fourth balloon 52. This mixed quadruple balloon of the axial torque type may be used in coronary angioplasty if it is constructed in an extremely small, flexible version; however, it is expected that the primary use of the catheter illustrated in FIG. 19 will be in peripheral vessel angioplasty.

G. Triple Concentric Balloon

In this triple balloon catheter design, all three balloons are concentrically mounted on the catheter shaft. As illustrated in FIG. 21, the first balloon 16 and the second balloon 20 are concentrically mounted on the catheter shaft 12 as in the double balloon catheter of FIG. 6. In addition, a third balloon 42, which is larger than the second balloon 20 and the first balloon 16, is mounted on top of the first balloon and the second balloon 20. It is preferred that the first balloon 16 and the second balloon 20 are completely inside the third balloon 42.

A central lumen 22 runs the length of the catheter shaft 12 and through the balloons 16, 20, 42, and, as in FIG. 6, the first and second lumens 24, 26 communicate with the interior of the first and second balloons 16, 20, respectively. A third lumen 28 is also provided in the catheter shaft 12, terminating in fluid connection with the interior of the third balloon 42 so that the third balloon 42 can be inflated and deflated by introducing fluid into and withdrawing fluid from the proximal end of the third lumen 28. The balloons 16, 20, 42 may be appropriately sized for either coronary or peripheral angioplasty.

As in FIG. 6, proximal holes 36 may be provied on the proximal side of the third balloon 42 and distal holes 40 may be provided on the distal side of third balloon 42. The holes 36, 40 are in fluid communication with the central lumen 22, permitting blood flow to bypass the balloons 16, 20, 42, by flowing through the central lumen.

The triple coaxial balloon may also be constructed in an axial torque design in which the distal end of all three balloons 16, 20, 42 is bonded directly to the axial torque guidewire 34, in the same manner as discussed in connection with FIG. 7.

II. SURGICAL PROCEDURE

In connection with the new catheter designs set forth above, a surgical procedure utilizing those balloons to permit multi-vessel coronary, peripheral, or valvular angioplasty in a greatly reduced time as compared to current techniques has been developed. This new percutaneous transluminal coronary angioplasty (PTCA) technique for multi-vessel disease is explained below in connection with representative schematic drawings illustrating particular locations of cardiovascular disease and a particular multiple balloon angioplasty catheter. Of course, it will be understood that the present technique can be utilized, in one form or another, with any of the catheter designs disclosed in the present application, and that utilization of the technique is not limited to the particular disease locations exemplified and illustrated in the following discussion and the accompanying figures. For illustration purposes only, a triple balloon catheter of the type illustrated in FIG. 14, without the bypass sideholes 36, 40, is shown in FIGS. 22-25.

A model of the left coronary system having multiple lesions in vessels of various diameter has been adpoted for purposes of this description. The diagrams used in this description, FIGS. 22-25, represent a hypothetical but not unrealistic case. It should be understood, of course, that the new surgical technique described herein can be used in either the left or the right coronary artery, or in both arteries, as a part of the same surgical procedure. What is critical for successful dilation of the lesions in question is that each dilation should be performed with a balloon having a predetermined maximum inflated diameter matching the diameter of the atherosclerotic native vessel.

Figure 22:
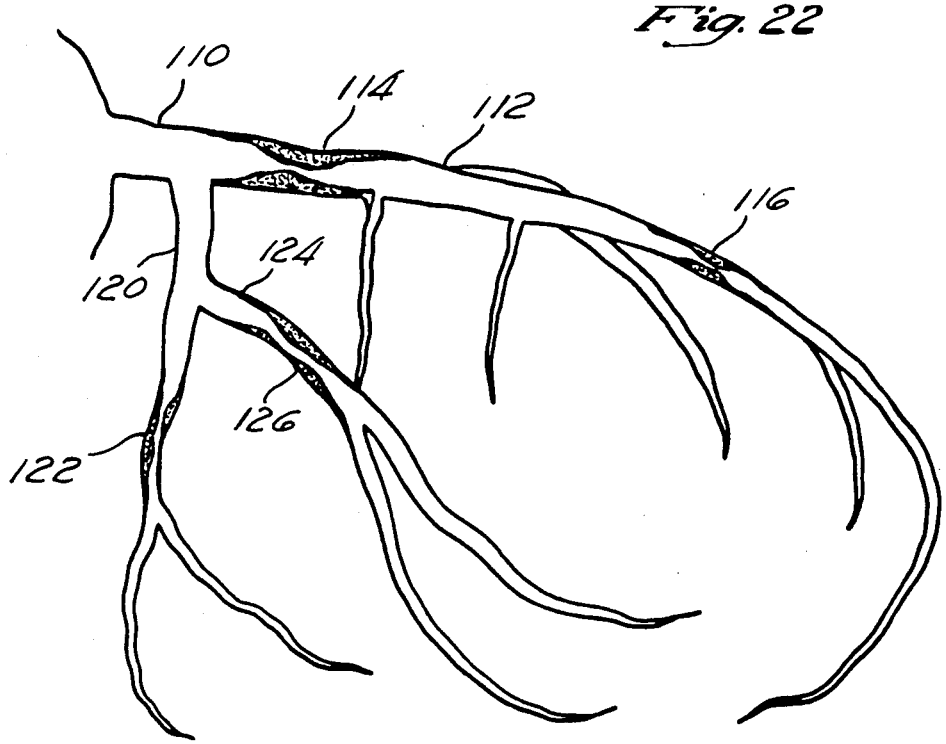
FIG. 22 is a diagram of the left coronary artery system.

FIG. 22 is a diagram of the left coronary artery system. The left main artery 110 branches into the left anterior descending (LAD) artery 112, in which two atherosclerotic lesions are illustrated. The first lesion 114 is located in the proximal portion of the LAD, in a vessel having a native diameter of 3.0 mm. The second lesion 116 is located in the distal LAD in a vessel having a native diameter of 2.0 mm. The circumflex artery 120 branches off of the left main artery 110. A third lesion 122 is illustrated in the circumflex artery 120, in a vessel having a native diameter of 2.0 mm. Finally, the obtuse marginal artery 124 (OMA) branches from the circumflex artery 120. A fourth lesion 126 is illustrated in the OMA 124 in a vessel having a native diameter of 2.5 mm.

With currently available PTCA techniques, three separate PTCA catheters would be needed to perform multi-vessel PTCA in this model. One of the catheters required would have a balloon of 3.0 mm, one a balloon of 2.5 mm, and one a balloon of 2.0 mm. With the procedure of the present invention, only one specially designed PTCA catheter is needed. As a result, the necessity for catheter exchange is eliminated, and the amount of X-ray exposure, the amount of contrast material injected, and the length of the PTCA procedure are all reduced.

The present invention may be used in the left coronary artery system having the lesions illustrated in FIG. 22 in the following way.

Figure 23:
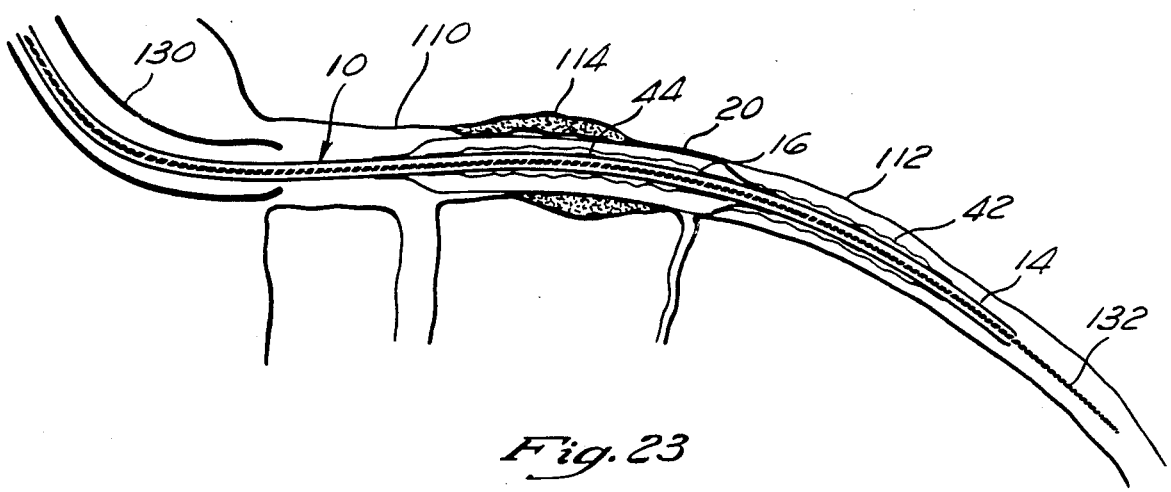
FIG. 23 is a diagram of the left anterior descending artery of FIG. 22, illustrating dilation of a stenosis.

With reference to FIG. 23, the patient is prepared and a conventional guiding catheter 130 is inserted through the aorta into the left main artery 110. Any suitable triple balloon catheter 10 of the type described previously herein is advanced through the guiding catheter and into the LAD 112. The triple balloon catheter 10 is provided with a first balloon 16 having a maximum inflated diameter of 2.5 mm, a second balloon 20 having a maximum inflated diameter of 3.0 mm, and a third balloon 42 having a maximum inflated diameter of 2.0 mm. The catheter 10 is preferably provided with a steerable, shapeable guidewire 132 of conventional design. The steerable guidewire 132 is used to guide the catheter 10 into the LAD, as in conventional PTCA. Of course, all three balloons 16, 20, 42 have been deflated with negative pressure as the catheter 10 is advanced into the first lesion 114 in the LAD 112.

When the second balloon 20 is properly positioned inside the first lesion 114, as verified by radiography showing the location of the radiopaque marker 44 inside the first and second balloons 16, 20, the 3.0 mm second balloon 20 is selectively inflated while the other balloons (16, 42) remain collapsed. Note that the distal third balloon 42 does not obstruct the lumen of the LAD 112 distal of the atherosclerotic lesion which is being dilated by the 3.0 mm second balloon 20. In FIG. 23, the second balloon 20 is illustrated in its fully inflated state, dilating the first lesion 114. When proper dilation of the lesion 114 has been achieved, the second balloon 20 is deflated by applying negative pressure to the second lumen (not shown). The balloon catheter is then advanced to the next target lesion with all three balloons 16, 20, 42, completely deflated.

Figure 24:
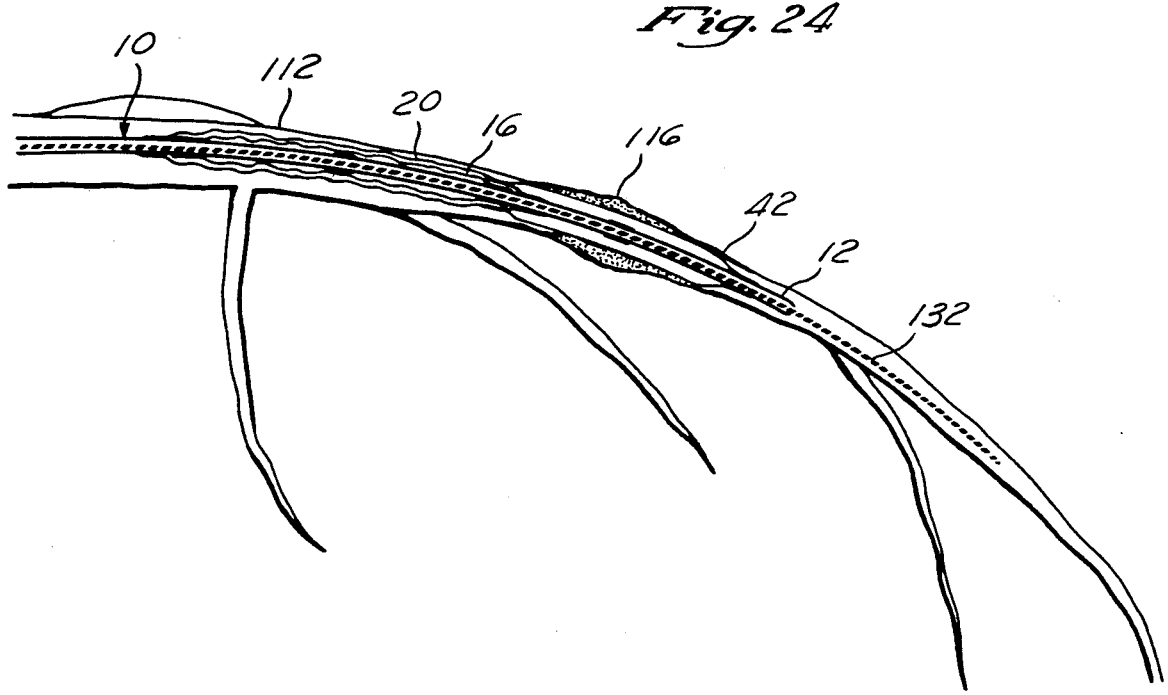
FIG. 24 is a diagram of the distal segment of the left anterior descending artery system of FIG. 22, illustrating dilation of a stenosis.

The balloon catheter 10 is next advanced distally into the LAD 112 until the 2.0 mm third balloon 42 is positioned inside the second lesion 116. Once the deflated 2.0 mm third balloon 42 is centered in the second lesion 116, the third balloon 42 is inflated to dilate the second lesion 116 as shown in FIG. 24, while the first and second balloons 16, 20 remain collapsed. Note that the deflated first and second balloons 16, 20 do not obstruct the artery lumen proximal to the atherosclerotic lesion 116 that is being dilated.

Figure 25:
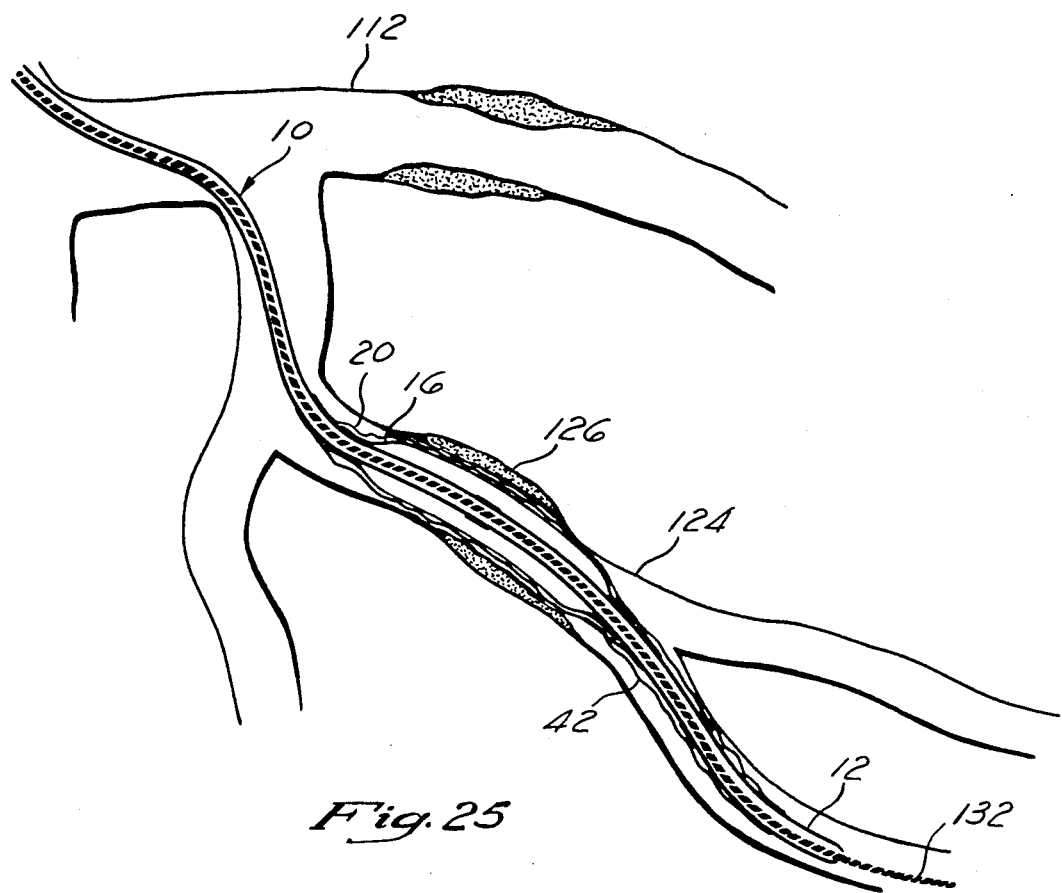
FIG. 25 is a diagram of the proximal obtuse marginal artery of FIG. 22, illustrating dilation of a stenosis.

When the lesion 116 has been fully dilated by inflation of the third balloon 42, negative pressure is applied to the third lumen (not shown) to fully deflate the third balloon 42. The catheter 10 is then retracted back to the left main artery 110 and, through use of the steerable guideware, is then threaded into the obtuse marginal artery 124, as shown in FIG. 25. Because the fourth lesion 126 in the obtuse marginal artery 124 is in a vessel having a native diameter of 2.5 mm, the first balloon 16 having a maximum inflated diameter of 2.5 mm is positioned inside the fourth lesion 126. The first balloon 16 is then fully inflated to dilate the lesion 126, while the second and third balloons 20 and 42, are fully collapsed by negative pressure. Note that the collapsed second balloon 20 is passively overlying the inflated first balloon 16 in FIG. 25. The catheter 10 is then collapsed and withdrawn from the obtuse marginal artery 124 and is inserted into the third lesion 122 in the circumflex artery 120 (not separately illustrated). The third lesion 122, in a vessel having a native diameter of 2.0 mm, is dilated with the third balloon 42 in the same manner as was described in connection with the second lesion 116.

The balloon catheter 10 and the guiding catheter 130 are then withdrawn and the procedure is completed in accordance with standard PTCA techniques.

Although the technique has been described in connection with the left coronary artery system, it is equally applicable in PTCA of the right coronary artery system and in peripheral and valvular angioplasty. Quadruple balloon catheters are particularly well suited for peripheral and valvular angioplasty.

Because both the right and the left coronary artery systems are equally susceptible to atherosclerotic disease, often patients will have disease in both coronary arteries at the same time. As long as the lesions are accessible to balloon angioplasty, they may be conveniently and efficiently dilated by the technique described herein using the multi-balloon catheter. The same balloon catheter can be used in both arteries. However, it will typically be necessary to exchange the guiding catheter if the procedure involves a shift from one artery to the other. The principle of effective balloon catheter utilization is the same in the two arteries. However, in order to increase efficiency, catheters changed from one artery to the other should be moved in such as way as to avoid a return to a vessel that has previously been entered. This is because each time the procedure is shifted from one artery to the other, it is necessary to exchange the guiding catheter.

The present invention permits full and effective dilation of some lesions that cannot effectively be dilated with a single balloon catheter. In some cases of advanced atherosclerotic disease, a lesion may result in such a reduced vessel diameter that a deflated angioplasty balloon having a maximum inflated diameter the same as the diameter of the native vessel cannot be advanced into the lesion. In this case, a multi-balloon catheter made in accordance with the present invention may be used to good effect. The low profile distal balloon on the catheter, having a deflated diameter less than the native lumen of the lesion, can be advanced into the lesion and inflated to partially dilate the lesion so that the appropriately-sized larger balloon can be placed inside the lesion and the lesion can be fully dilated. Thus, tight lesions can be predilated with a small balloon first, so that dilation of the lesions can be completed with the larger balloon. It is estimated that 20–25% of the single lesion cases in which balloon angioplasty is now performed currently require a second balloon catheter because the originalselected balloon catheter is too large to cross the lesion. With the present invention, these constricted single-lesion dilations can now be performed with a single multi-balloon catheter.

In summary, the procedure of the present invention requires advancing a multi-balloon angioplasty catheter having a plurality of differently-sized balloons into the vessel to be dilated, dilating a first lesion with a balloon having a first diameter, dilating a second lesion with a balloon having a second diameter, and, optionally, dilating a third lesion with a third balloon having a predetermined third diameter appropriate for the third lesion. With each dilation, only the dilating balloon is inflated.

In accordance with another aspect of the procedure of the present invention, a single lesion may be dilated with a multi-balloon catheter by advancing a first balloon having a predetermined first diameter into the lesion, and dilating the lesion by inflating only the first balloon, and then advancing a second balloon into the lesion, wherein the second balloon has a maximum inflated diameter larger than the maximum inflated diameter of the first balloon, and then dilating the lesion by inflating only the second balloon.

What is claimed is:

1. A catheter for performing balloon angioplasty, comprising:
   an elongate, flexible catheter shaft having at least two lumens therethrough;
   at least two relatively inelastic angioplasty balloons on said shaft, wherein said balloons are connected to separate lumens for independent inflation and deflation thereof, and each of said balloons has a predetermined maximum inflated diameter and is adapted to dilate a stenosis when inflated;
   said balloons comprising:
   a first balloon;
   a second balloon on top of said first balloon, so that said first balloon is inside said second balloon, wherein the maximum inflated diameter of said first balloon is less than the maximum inflated diameter of said second balloon so that when said first balloon and said second balloon are fully both inflated, said first balloon is spaced radially inwardly from said second balloon;
   a central lumen extending longitudinally through said catheter shaft; and
   a steerable guidewire extending through said central lumen.

2. The catheter of claim 1, wherein said first balloon is completely inside said second balloon.

3. The catheter of claim 1, further comprising means for permitting the flow of blood through said catheter shaft past said balloons.

4. A catheter for performing balloon angioplasty, comprising:
   an elongate, flexible catheter shaft having at least two lumens therethrough;
   at least two relatively inelastic angioplasty balloons on said shaft, wherein said balloons are connected to separate lumens for independent inflation and deflation thereof, and each of said balloons has a predetermined maximum inflated diameter and is adapted to dilate a stenosis when inflated;
   said balloons comprising:
   a first balloon;

a second balloon on top of said first balloon, so that said first balloon is inside said second balloon, wherein the maximum inflated diameter of said first balloon is less than the maximum inflated diameter of said second balloon; and an axial torque guidewire extending through said catheter shaft and out of the distal end thereof, wherein the proximal ends of said first balloon and said second balloon are bonded to the distal end of said catheter shaft and wherein the distal ends of said first balloon and said second balloon are bonded to said wire.

5. A catheter for performing balloon angioplasty, comprising:

an elongate, flexible catheter shaft having at least two lumens therethrough;

at least two relatively inelastic angioplasty balloons on said shaft, wherein said balloons are connected to separate lumens for independent inflation and deflation thereof, and each of said balloons has a predetermined maximum inflated diameter and is adapted to dilate a stenosis when inflated;

said balloons comprising:

a first balloon;

a second balloon on top of said first balloon, so that said first balloon is inside said second balloon, wherein the maximum inflated diameter of said first balloon is less than the maximum inflated diameter of said second balloon; and a third balloon on top of said second balloon, so that said second balloon is at least partially inside said third balloon, wherein the maximum inflated diameter of said second balloon is less than the maximum inflated diameter of said third balloon.

6. The catheter of claim 5, wherein said first balloon is completely inside said second balloon and said second balloon is completely inside said third balloon.

7. The catheter of claim 5, further comprising an axial torque guidewire extending through said catheter shaft and extending out of the distal end of said catheter shaft, wherein the distal ends of said first, second, and third balloons are bonded to said wire.

8. The catheter of claim 5, wherein the catheter shaft extends through said first, second, and third balloons, further comprising a central lumen extending through said catheter shaft for receiving an steerable guidewire.

9. The catheter of claim 5, further comprising means for permitting the flow of blood through the catheter shaft past said balloons.

10. A catheter for performing balloon angioplasty, comprising:

an elongate, flexible catheter shaft having at least two lumens therethrough;

at least two relatively inelastic angioplasty balloons on said shaft, wherein said balloons are connected to separate lumens for independent inflation and deflation thereof, and each of said balloons has a predetermined maximum inflated diameter and is adapted to dilate a stenosis when inflated;

said balloons comprising:

a first balloon;

a second balloon on top of said first balloon, so that said first balloon is inside said second balloon, wherein the maximum inflated diameter of said first balloon is less than the maximum inflated diameter of said second balloon; and a third balloon on said catheter shaft distal of but adjacent to said first and second balloons, wherein the maximum inflated diameter of said third balloon is smaller than the maximum inflated diameter of said first balloon.

11. A catheter of claim 10, further comprising an axial torque guidewire extending through said catheter shaft and extending out of the distal end of said catheter shaft, wherein the distal end of said third balloon is bonded to said wire.

12. The catheter of claim 10, wherein the catheter shaft extends through said first, second, and third balloons, further comprising a central lumen extending through said catheter shaft for receiving a steerable guidewire.

13. The catheter of claim 12, further comprising means for permitting the flow of blood through the catheter shaft past said balloons.

14. The catheter of claim 10, further comprising an attachment site on said catheter shaft to which the proximal end of said third balloon and the distal end of said second balloon are joined, wherein one of said second balloon and said third balloon has been formed to permanently prolapse at least partially over said attachment site.

15. The catheter of claim 14, further comprising an axial torque guidewire extending through said catheter shaft and extending out of the distal end of said catheter shaft, wherein the distal end of said third balloon is bonded to said wire.

16. The catheter of claim 14, wherein the catheter shaft extends through said first, second, and third balloons, further comprising a central lumen extending through said catheter shaft for receiving a steerable guidewire.

17. The catheter of claim 14, further comprising means for permitting the flow of blood through the catheter shaft past said balloons.

18. The catheter of claim 10, wherein said second balloon and said third balloon are formed of a single, continuous tube of polymer material.

19. The catheter of claim 10, wherein said first balloon and said third balloon are formed of a single, continuous tube of balloon material.

20. The catheter of claim 10, further comprising an attachment site on said catheter shaft to which the distal end of said second balloon is attached, wherein the proximal end of said third balloon is attached to the wall of said second balloon proximally of said attachment site on said catheter shaft.

21. The catheter of claim 20, further comprising an axial torque guidewire extending through said catheter shaft and extending out of the distal end of said catheter shaft, wherein the distal end of said third balloon is bonded to said wire.

22. The catheter of claim 20, wherein the catheter shaft extends through said first, second, and third balloons, further comprising a central lumen extending through said catheter shaft for receiving a steerable guidewire.

23. The catheter of claim 22, further comprising means for permitting the flow of blood through the catheter shaft past said balloons.

24. The catheter of claim 10, further comprising a fourth balloon on top of said third balloon, so that said third balloon is at least partially inside said fourth balloon, wherein the maximum inflated diameter of said fourth balloon is greater than the maximum inflated diameter of said third balloon, but less than the maximum inflated diameter of said first balloon.

25. The catheter of claim 24, further comprising an axial torque guidewire extending through said catheter shaft and extending out of the distal end of said catheter shaft, wherein the distal end of said third balloon and the distal end of said fourth balloon are bonded to said wire.

26. The catheter of claim 24, wherein the catheter shaft extends through said first, second, third, and fourth balloons, further comprising a central lumen extending through said catheter shaft for receiving a steerable guidewire.

27. The catheter of claim 24, further comprising means for permitting the flow of blood through the catheter shaft past said balloons.

28. The catheter of claim 10, further comprising a fourth balloon distal of but adjacent to said third balloon, wherein the maximum inflated diameter of said fourth balloon is smaller than the maximum inflated diameter of said third balloon.

29. The catheter of claim 28, further comprising an axial torque guidewire extending through said catheter shaft and extending out of the distal end of said catheter shaft, wherein the distal end of said fourth balloon is bonded to said wire.

30. The catheter of claim 28, wherein the catheter shaft extends through said first, second, third, and fourth balloons, further comprising a central lumen extending through said catheter shaft for receiving a steerable guidewire.

31. The catheter of claim 28, further comprising means for permitting the flow of blood through the catheter shaft past said balloons.

32. The catheter of claim 28, further comprising a first attachment site on said catheter shaft to which the distal end of said second balloon is attached and a second attachment site on said catheter shaft to which the distal end of said third balloon is attached, wherein the proximal end of said third balloon is bonded to the wall of said second balloon distally of said first attachment site, and wherein the proximal end of said fourth balloon is bonded to the wall of said third balloon distally of said second attachment site. diameter of said second balloon is less than the maximum inflated diameter of said third balloon.

33. The catheter of claims 1, 4, 10, 16, 21, 24, or 29, wherein said balloons are capable of substantially maintaining said predetermined maximum inflated diameter at inflation pressures of 150 psi.

34. The catheter of claims 1, 4, 10, 16, 21, 24, or 29, further comprising a radiopaque marker on said catheter at the longitudinal location of said first balloon.

35. The catheter of claims 10, 14, 20, 25, or 28, further comprising a radiopaque marker on said catheter at the longitudinal location of said third balloon.

36. The catheter of claims 1, 4, 10, 16, 21, 24, or 29, wherein the length of each of said balloons does not exceed 40 mm.

37. The catheter of claims 1, 4, 10, 14, 20, 25, 28, or 5, wherein the maximum inflated diameter of each of said balloons does not exceed about 4.5 mm.

38. The catheter of claims 1, 4, 10, 14, 20, 25, 28, or 5, wherein the length of each of said balloons does not exceed about 80 mm.

39. The catheter of claims 1, 4, 10, 14, 20, 25, 28, or 5, wherein the maximum inflated diameter of each of said balloons does not exceed about 15 mm.

40. The catheter of claims 1, 4, 10, 14, 20, 25, 28, or 5, wherein, when said balloons are deflated, the diameter of said catheter through said balloons does not exceed about 2.0 mm.

41. A method for performing balloon angioplasty, comprising the steps of:
selecting an angioplasty catheter having thereon a separately-inflatable first balloon with a first predetermined maximum inflated diameter and a separately-inflatable second balloon with a different, second maximum inflated diameter that is larger than said first diameter, wherein said first balloon is at least partially inside said second balloon;
positioning said first balloon inside a first stenosis in a blood vessel or a heart valve and inflating said first balloon to dilate said first stenosis; and
positioning said second balloon inside a second stenosis in a blood vessel or a heart valve and inflating said second balloon to dilate said second stenosis, wherein the predetermined maximum inflated diameter of said first balloon is approximately equal to the diameter of the native vessel in which said first stenosis is located and wherein the predetermined maximum inflated diameter of said second balloon is approximately equal to the diameter of the native vessel in which the second stenosis is located.

42. The method of claim 41, further comprising the step of deflating said first balloon after dilating said first stenosis but before dilating said second stenosis.

43. The method of claim 41, wherein said first stenosis and said second stenosis are atherosclerotic stenoses.

44. The method of claim 42, wherein said vessels are coronary arteries.

45. The method of claim 41, wherein said angioplasty catheter has a separately-inflatable third balloon thereon, wherein said third balloon has a maximum inflated diameter different from that of said first balloon or said second balloon, further comprising the steps of:
positioning said third balloon inside a third stenosis in a blood vessel; and
inflating said third balloon to dilate said third stenosis.

46. The method of claim 45, wherein said first stenosis, said second stenosis, and said third stenosis are atherosclerotic stenoses.

47. The method of claim 45, wherein the predetermined maximum inflated diameter of said first balloon is approximately equal to the diameter of the native vessel in which said first stenosis is located, the predetermined maximum inflated diameter of said second balloon is approximately equal to the diameter of the native vessel in which the second stenosis is located, and the predetermined maximum inflated diameter of said third balloon is approximately equal to the diameter of the native vessel in which the third stenosis is located.

48. The method of claim 47, wherein said vessels are coronary arteries.

49. A method for performing balloon angioplasty, comprising the steps of:
selecting an angioplasty catheter having a separately-inflatable first balloon with a first predetermined maximum inflated diameter and a second separately-inflatable balloon having a different, larger predetermined maximum inflated diameter than said first balloon, wherein said first balloon is at least partially inside second balloon;
positioning said first balloon and said second balloon inside a stenosis inside a blood vessel or valve;
inflating said first balloon to partially dilate said stenosis while maintaining said positioning; and inflating said second balloon to further dilate said stenosis while maintaining said positioning.

50. The method of claim 49, wherein the maximum inflated diamter of said second balloon is approximately equal to the diameter of the native vessel in which said stenosis is located.

51. The method of claim 49, wherein said vessels are coronary arteries.

52. A method for performing balloon angioplasty, comprising the steps of:

selecting an angioplasty catheter having a first separately-inflatable balloon with a first predetermined maximum inflated diameter and a second separately-inflatable balloon having a different, larger predetermined maximum inflated diameter than said first balloon, wherein said first balloon is located on said catheter distally of said second balloon, said balloons having walls, and wherein one of said balloons is attached to the wall of another of said balloons;

positioning said first balloon inside a stenosis inside a blood vessel or valve;

inflating only said first balloon to partially dilate said stenosis;

advancing said second balloon into said partially-dilated stenosis; and inflating only said second balloon to further dilate said stenosis.

* * * * *